US008709338B2

(12) United States Patent
Bates et al.

(10) Patent No.: US 8,709,338 B2

(45) Date of Patent: Apr. 29, 2014

(54) METHODS AND APPARATUS FOR ULTRASONIC CLEANING

(75) Inventors: Darren M Bates, Twin Waters (AU); Andrew Sin Ju Yap, Gawler (AU); Arthur R Mcloughlin, Panorama (AU)

(73) Assignee: Cavitus Pty Ltd, North Sydney (AU)

( * ) Notice: Subject to any disclaimer, the term of this patent is extended or adjusted under 35 U.S.C. 154(b) by 451 days.

(21) Appl. No.: 12/991,250

(22) PCT Filed: May 8, 2009

(86) PCT No.: PCT/AU2009/000584

§ 371 (c)(1), (2), (4) Date: Feb. 23, 2011

(87) PCT Pub. No.: WO2009/135273

PCT Pub. Date: Nov. 12, 2009

(65) Prior Publication Data

US 2011/0135534 A1 Jun. 9, 2011

(30) Foreign Application Priority Data

| | | |
|---|---|---|
| May 8, 2008 | (AU) | 2008902236 |
| Oct. 24, 2008 | (AU) | 2008905501 |
| Oct. 24, 2008 | (AU) | 2008905502 |

(51) Int. Cl.

| | |
|---|---|
| ***B08B 17/00*** | (2006.01) |
| ***A61L 2/00*** | (2006.01) |
| ***B06B 1/00*** | (2006.01) |

(52) U.S. Cl.

USPC ...... 422/20; 422/1; 422/6; 422/127; 422/128; 134/1

(58) Field of Classification Search

USPC ........ 422/1, 6, 127–128, 20; 134/1, 184, 186, 134/201, 14, 161, 164; 310/334, 367; 15/77, 88

See application file for complete search history.

(56) References Cited

U.S. PATENT DOCUMENTS

| | | | | |
|---|---|---|---|---|
| 4,710,233 | A | 12/1987 | Hohmann et al. | |
| 5,994,818 | A * | 11/1999 | Abramov et al. | 310/325 |
| 6,178,974 | B1 | 1/2001 | Kobayashi et al. | |
| 6,585,826 | B2 * | 7/2003 | Tai et al. | 134/3 |
| 2002/0185150 | A1 * | 12/2002 | Namerikawa et al. | 134/1 |
| 2006/0191424 | A1 | 8/2006 | McLoughlin et al. | |

FOREIGN PATENT DOCUMENTS

| | | |
|---|---|---|
| JP | 11179305 | 7/1999 |

OTHER PUBLICATIONS

Jiranek, V. et al. High power ultrasonics as novel tool offering new opportunities for managing wine microbiology, Springer Science + Business Media B.V. 2007 [online], Published online Sep. 6, 2007.

"Brettanomyces: friend or foe? A masterclass with Matt Thomson, winemaker" http://www.wineandcork.com/brettanomyces_masterclass.htm. Nov. 2007.

* cited by examiner

*Primary Examiner* — Monzer R Chorbaji

(74) *Attorney, Agent, or Firm* — Honigman Miller Schwartz & Cohn, LLP; Thomas A. Wootton; Jennifer P. O'Brien

(57) ABSTRACT

The present invention relates to a method of cleaning a surface by applying highly propagating ultrasonic energy to said surface, the method comprises immersing at least a portion of the surface into a fluid, wherein said fluid is in contact with an highly propagating ultrasonic energy emitting assembly; and emitting highly propagating ultrasonic energy from the assembly into the fluid to generate cavitation at the surface thereby cleaning said surface.

15 Claims, 13 Drawing Sheets

METHODS AND APPARATUS FOR ULTRASONIC CLEANING

CROSS-REFERENCE TO RELATED APPLICATION

This application is the U.S. National phase of PCT Application No. PCT/AU2009/000584, filed May 8, 2009, which claims the priority of Australian Application Serial No. 2008905501, filed Oct. 24, 2008, Australian Application Serial No. 2008905502, filed Oct. 24, 2008, and Australian Application Serial No. 2008902236 filed May 8, 2008, all of which are incorporated herein by reference in their entirety.

TECHNICAL FIELD

The present invention relates to methods of ultrasonic cleaning and disinfection. In particular the invention relates to methods of ultrasonic cleaning and disinfection via the application of highly propagating ultrasonic energy to a surface to be cleaned and/or disinfected.

BACKGROUND

Equipment, containers, packaging and foodstuffs provide surfaces for the accumulation of detritus and surfaces for microorganism colonisation and growth. This accumulation of detritus and microorganism growth can cause fouling and reduce the efficiency of the equipment, the quality of the product produced using that equipment and reduce the life of equipment, containers and packaging. Furthermore, microorganism growth leads to premature spoilage of products, particularly foodstuffs or cross-contamination with micro organisms causing food borne illness. Microorganism biofilms resistant to inadequate nutrient supply, drying, adverse temperature, abrasion or chemicals may form on surfaces of foodstuffs, containers or equipment such as condensors, heat exchangers, valves, pipes, vessels, air cooling towers or any surface exposed to moisture. Such contamination fouling or biofilms lead to spoilage of the foodstuffs, micro-organisms causing food borne illness or fouling of the containers or equipment.

Typically, spoilage is delayed by use of packaging materials, hygienic processing to reduce the load of spoilage organisms and refrigeration. However, these methods do not actively remove spoilage organisms. In addition, conventional washing processes do not remove microorganisms within a surface or adequately remove detritus tightly bound to a surface.

Contaminating microorganisms, biofilms and/or detritus are typically reduced using any one of a number of methods including washing, chemical treatments or physical removal. Washing with low or high pressure (680 to 2684 kPa), cold or warm water (60 to 82° C.) removes soft, but not hard deposits and provides limited surface disinfection. Steam cleaning is more efficient but will not disinfect the surface layers to the same depth that microorganism growth occurs and is not suitable for foodstuffs. Poor thermal conductivity through detritus inhibits heat transfer and thus microorganism elimination.

Chemical cleaning agents may dissolve surface detritus during cleaning although neutralising washes after such treatment is required. However, such chemicals have poor mass transfer effect through solid detritus and into surface layers of containers or other structures including fruits and vegetables. Thus, these methods result in poor reduction of microorganism load. Physical methods of cleaning and surface disinfection such as shaving, dry ice particle bombardment merely treat the surface and do not remove microorganisms deeper into the structure. Harsh physical methods and are not applicable to foodstuffs.

Conventional ultrasonic cleaning apparatus and methods have been utilised to clean a wide variety of material, including containers. However, the ultrasonic energy produced in a conventional apparatus creates standing waves so that the pattern of cleaning results in alternating partially cleaned zones in areas not bounded by the standing waves and uncleaned zones in the regions bounded by the standing waves. Furthermore, ultrasonic energy produced in a conventional apparatus does not penetrate into a surface and propagates only for a very short distance. In order to clean an article it must be moved relative to the standing wave which can be impractical for large articles.

Accordingly there exists a need in the art for apparatus and methods for improved cleaning and/or disinfection of surfaces.

SUMMARY

According to a first aspect of the present invention, there is provided a method of cleaning a surface by applying highly propagating ultrasonic energy to said surface, the method comprises immersing at least a portion of the surface into a fluid, wherein said fluid is in contact with an highly propagating ultrasonic energy emitting assembly; and emitting highly propagating ultrasonic energy from the assembly into the fluid to generate cavitation at the surface thereby cleaning said surface.

According to a second aspect of the present invention, there is provided a method of removing a contaminant from a surface the method comprises immersing at least a portion of the contaminant into a fluid wherein said fluid is in contact with an highly propagating ultrasonic energy emitting assembly; and emitting highly propagating ultrasonic energy from the assembly into the fluid to generate cavitation at the surface thereby removing said contaminant.

In one embodiment, the contaminant may be a biofilm, scale or tartrate.

According to a third aspect of the present invention there is provided a method of disinfecting a surface, the method comprises immersing at least a portion of the surface into a fluid wherein said fluid is in contact with an ultrasonic sonotrode; and emitting highly propagating ultrasonic energy from the sonotrode into the fluid to generate cavitation at the surface thereby disinfecting said surface.

According to a fourth aspect of the present invention, there is provided a method for ultrasonic cleaning of a surface of a first container using highly propagating ultrasonic energy, the method comprises:

placing a fluid in contact with at least a portion of the surface of the first container wherein said fluid is contained within a second container, and placing a highly propagating ultrasonic energy emitting assembly in contact with a fluid in the second container or in contact with a surface of said second container;

emitting highly propagating ultrasonic energy from said assembly and applying said energy to clean the surface of the first container.

In one embodiment, the method further comprises generating cavitation at the surface of said first container thereby cleaning said surface.

In one embodiment the method further comprises disinfecting the portion of the surface of the first container by the application of highly propagating ultrasonic energy.

In one embodiment the method further comprises rotating the first container relative to the second container to place the fluid in contact with another portion of the surface of the first container.

In one embodiment the method further comprises removing lees from the first container.

According to a fifth aspect of the present invention, there is provided a method to clean a surface having detritus, the method comprises:

introducing the surface to a fluid;

introducing an highly propagating ultrasonic energy emitting assembly to the fluid;

emitting highly propagating ultrasonic energy from said assembly during rotation of the surface to expose the surface layers of the inner surface to ultrasonic energy; and applying said energy to remove detritus from said surface.

In one embodiment the surface is present in a container such as a barrel. The barrel may be a wooden wine barrel. The detritus may be a biofilm or food product residue including wine residue such as tartrate or scale. The detritus may be a spoilage microorganism.

In one embodiment the fluid may at least partially fill the container. The emitting assembly may be introduced to the fluid through an opening in the container such as an open head of the barrel.

In another embodiment operating the emitting assembly creates cavitation within the fluid. In another embodiment the cavitations generate heat in the fluid.

In another embodiment the fluid may contain a chemical sanitizer and/or a cleaning agent. In another embodiment the method further comprises the step of applying a pulsed electric field to the fluid. In yet another embodiment the method further comprises mechanical brushing of the surface.

In one embodiment the heat and cavitation acts synergistically to clean, remove the biofilm and/or disinfect the surface. In another embodiment the cavitation and pulsed electric field act synergistically to disinfect, clean and/or remove the biofilm from the surface. In another embodiment the cavitation and mechanical abrasion act synergistically to disinfect, clean and/or remove the biofilm from the surface.

In a further embodiment the method further comprises positioning the ultrasonic energy emitting assembly in communication with a transducer. For example, the sonotrode is in contact with the transducer.

According to a sixth aspect of the present invention, there is provided a system for cleaning a surface using highly propagating ultrasonic energy, the system comprises:

means for placing a fluid in contact with at least a portion of the surface;

means for placing an highly propagating ultrasonic energy emitting assembly in contact with the fluid; and wherein during operation said assembly emits highly propagating ultrasonic energy into the fluid to generate cavitation in the surface thereby cleaning said surface.

In one embodiment the means for operating the emitting assembly comprises means for operating the ultrasonic energy emitting assembly to generate ultrasonic cavitation within the fluid and clean the surface.

In another embodiment operation of said highly propagating ultrasonic energy emitting assembly results in emission of highly propagating ultrasonic energy into the fluid to generate cavitation in the surface thereby disinfecting the surface by destroying spoilage microorganisms.

The spoilage microorganisms may be selected from the group comprising yeasts, moulds, bacteria, fungi. In one embodiment the yeast is a species of the *Brettanomyces* genus.

In yet another embodiment the system further comprises a means for rotating the surface to place the fluid in contact with another portion of the surface.

In a further embodiment the system further comprises a means for removing lees.

According to a seventh aspect of the present invention there is provided a highly propagating ultrasonic energy apparatus for cleaning a surface of a first container, the apparatus comprises:

at least one immersible highly propagating ultrasonic energy transducer assembly mounted to a second container adapted to be placed within the first container a highly propagating ultrasonic energy generator in communication with the transducer assembly.

In one embodiment the second container may be adapted to be placed within the first container through an open end such as an open end of a barrel from which the head stave has been removed.

In one embodiment the second container may be a polygon sided cylinder. The cylinder may be sealed.

The second container may have a volume equal to between about 5% and about 95% of the internal volume of the first container, but preferably about 70% of the volume of said first container.

According to an eighth aspect of the present invention there is provided a highly propagating ultrasonic energy apparatus for cleaning a surface of a first container, the apparatus comprises:

at least one highly propagating ultrasonic energy emitting assembly mounted to a second container wherein said second container is adapted to contain a liquid and receive at least a portion of said surface to be cleaned in said liquid, and a highly propagating ultrasonic energy generator in communication with the energy emitting assembly.

In one embodiment the ultrasonic energy emitting assembly is mounted to an internal or external surface of the second container.

In one embodiment the highly propagating ultrasonic energy emitting assembly comprises a sonotrode. In one embodiment the sonotrode emits highly propagating ultrasonic energy radially. In another embodiment operation of said highly propagating ultrasonic energy emitting assembly results in emission of highly propagating ultrasonic energy into the fluid to generate cavitation in the surface. The cavitation enhances fluid entry into the surface thereby enabling further cavitation in the surface.

In one embodiment the fluid is a gas or liquid such as water.

In one embodiment the apparatus further comprises an ultrasonic energy sensor adapted to indicate an amount of ultrasonic energy.

In another embodiment the ultrasonic energy emitting assembly comprises of a plurality of materials such as titanium and titanium alloys.

In one embodiment the apparatus may comprise a third container be adapted to be placed within the first container for example through an open end such as an open end of a barrel from which the head stave has been removed.

In one embodiment the third container may be a polygon sided cylinder. The cylinder may be sealed.

The third container may have a volume equal to between about 5% and about 95% of the internal volume of the first container, but preferably about 70% of the volume of said first container.

According to a ninth aspect of the present invention there is provided a use of the system of the sixth aspect or the apparatus of the seventh or eighth aspects for cleaning a surface.

DEFINITIONS

The term "highly propagating ultrasonic energy" includes within its meaning ultrasonic energy emitted substantially orthogonal to the axial direction of a sonotrode.

The term "comprising" means including principally, but not necessarily solely. Furthermore, variations of the word "comprising", such as "comprise" and "comprises", have correspondingly varied meanings.

As used in this application, the singular form "a", "an" and "the" include plural references unless the context clearly dictates otherwise. For example, the term "a surface" also includes a plurality of surfaces.

As used herein, the term "synergistic" refers to a greater than additive effect that is produced by a combination of two entities. A synergistic effect exceeds that which would be achieved by combining the effect of each entity taken alone.

The term "surface" as used herein includes within its meaning the boundary of an object or layer constituting or resembling such a boundary. That is, as used herein the term "surface" refers to the two-dimensional surface of an object and within the surface layer, up to a depth of about 1-20 mm, or up to a depth of about 2-20 mm or up to a depth of about 5-20 mm or up to a depth of about 5-15 mm or up to a depth of about 7-10 mm.

DESCRIPTION

The skilled person will understand that the figures and example provided herein are to exemplify, and not to limit the invention and its various embodiments.

Figure 1:
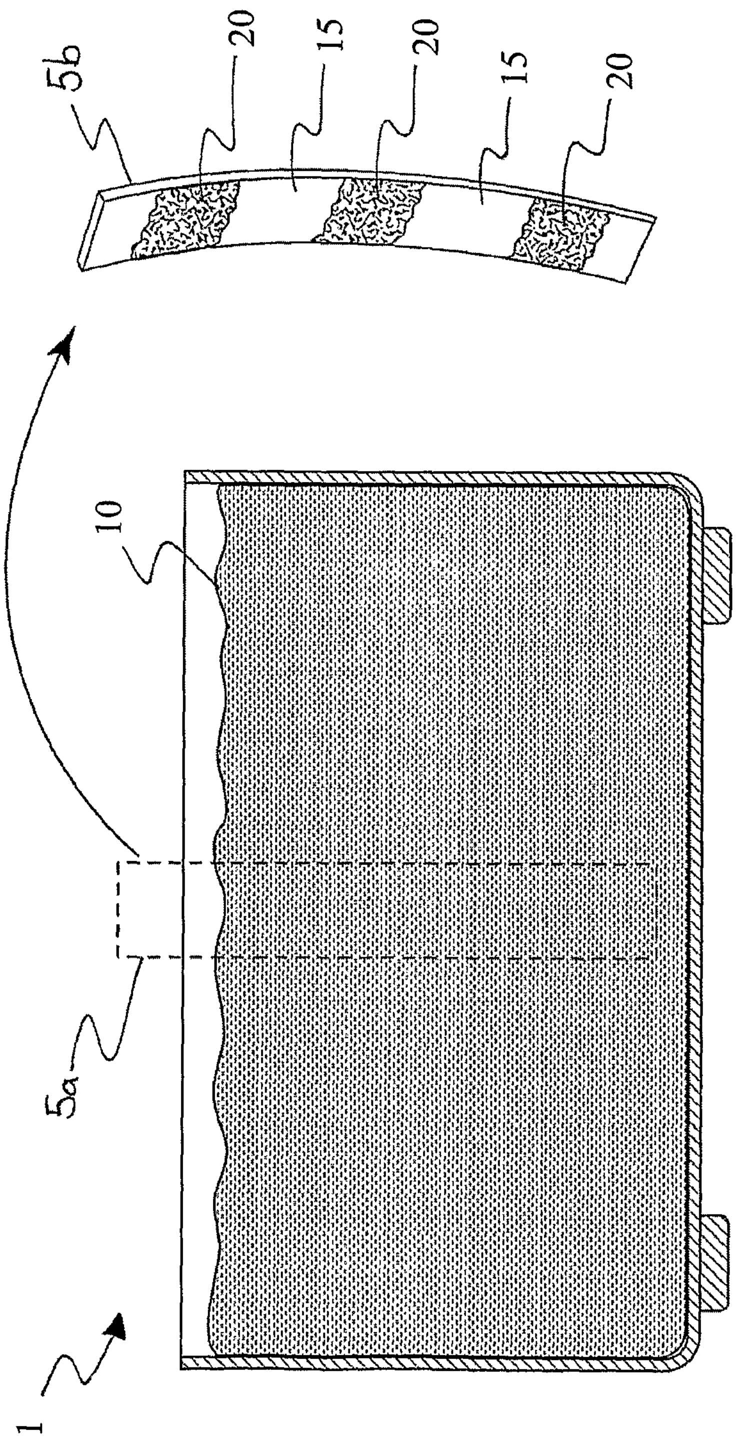
FIG. 1 is a view of a prior art standing wave device and the resultant effect.

Conventional ultrasonic cleaning apparatus, such as the apparatus 1 illustrated in FIG. 1 and methods have been utilised to clean a wide variety of material, including containers and barrel staves 5. Use of conventional ultrasonic apparatus 1 to clean a barrel stave 5 typically requires immersion of the barrel stave 5*a* in a liquid 10 which fills the apparatus 1. However, the ultrasonic energy produced in a conventional apparatus 1 creates standing waves in the liquid 10 filling the apparatus 1 so that when removed from the apparatus the barrel stave 5*b* shows a pattern of alternating partially cleaned zones 15 in areas not bounded by the standing waves and uncleaned zones 20 in the regions bounded by the standing waves.

In accordance with the present invention apparatus and methods for applying highly propagating ultrasonic energy to a surface are provided. The apparatus generally comprise an ultrasonic generator, at least one ultrasonic transducer arranged such that highly propagating ultrasonic energy is applied to a surface via a fluid. The methods of the invention generally comprise the application of highly propagating ultrasonic energy to a surface for the removal of solid or semi-solid waste material from the surface and for the inactivation of killing of microorganisms on a surface or within the structure that forms that surface.

For example, the surface may be the surface of an article, such as a container, conduit, device or foodstuff. The container may be a wine barrel; for example a wine barrel with tartrate deposits. The conduit may be a pipe. The device may be a heat exchanger, valve, tap, radiator, filters, washing flume, thermal pasteurizer tubes, mixers, homogenizers, filler bowls on packaging lines, membrane filters, tanks, hoppers, packaging materials, bottles/cans/cartons, filler nozzles, dispensers, evaporators, cookers, decanters, separation vessels, centrifuges, or grinders. The foodstuff may be a fruit or a vegetable.

Conventional ultrasonic cleaning bath technology/transducers are based on the formation of standing wave technology. Standing waves do not penetrate into solid substrates as the energy levels are very low. Similarly standing waves do not enhance liquid mass transfer or convective heat transfer. Furthermore the formation of standing waves results in areas exposed to the standing waves and areas that are not exposed, typically giving a 50% dead zone. Thus, in a container like an oak barrel, the result may be that only 50% of the surface is cleaned in terms of tartrate removal. Additionally as standing waves do not penetrate the surface far less than 50% of the microorganism load may be removed. Furthermore, due to the low energy levels removal of detritus such as tartrate is minimal and little, if any, tartrate is removed from the areas exposed to the standing wave.

Existing sonotrode technology produces waves of very limited propagation distance with no possibility of penetration into solid materials. Conventional systems produce energy waves that dissipate very quickly with distance and do not affect the liquid mass transfer properties of a fluid and the convective heat transfer properties. For example, a conventional sonotrode experiences a drop in energy of approximately 95% over 1 m from the sonotrode, with negligible penetration into surrounding material. The treated zone from these waves produced is not effective across a contaminated surface area—that is cavitation occurs in some areas and not in others.

The use of highly propagating ultrasonic energy waves provide improvements over existing ultrasonic cleaning technology and sonotrode systems which include, for example:

1. enhanced working/travel distance of energy waves
2. energy of waves maintained at long distances
3. ability of energy waves to penetrate solid porous materials
4. enhanced liquid mass transfer and convective heat transfer Highly Propagating Ultrasonic Energy A sonotrode generates ultrasonic energy typically when an alternating voltage is applied across a ceramic or piezoelectric crystalline material (PZT). The alternating voltage is applied at a desired oscillation frequency to induce movement of the PZT. The PZT transducer is mechanically coupled to the horn means which amplifies the motion of the PZT. The horn means includes a tip portion, referred to herein as a sonotrode. The assembly of the PZT horn means including the tip portion may also be referred to herein as the sonotrode. Highly propagating ultrasonic energy includes ultrasonic energy that is emitted substantially orthogonal to the axial direction of a sonotrode. Such energy propagates through a fluid medium, typically water or a gas and over a large distance from the sonotrode and is not limited to the areas immediately surrounding the sonotrode. After propagating through the medium the highly propagating ultrasonic energy may be applied over a surface and to penetrate into said surface.

Highly propagating ultrasonic energy waves are able to propagate across a fluid boundary such as water up to a distance of at least 50 cm to about 300 cm, or about 100 cm to about 300 cm or about 150 cm to about 300 cm or about 200 cm to about 300 cm to a contaminated surface. Highly propagating ultrasonic energy propagates substantially uniformly across surface areas and volumes leaving and is able to penetrate up to up to a depth of about 1-20 mm, or up to a depth of about 2-20 mm or up to a depth of about 5-20 mm or up to about 5-15 mm or up to about 7-10 mm into a solid, porous or contaminated surface.

In one embodiment of the present invention a combination of the high power, low frequency, long wavelength and sonotrode shape/design allows for the above effects to take place. In contrast, ultrasonic energy emitted from conventional ultrasonic cleaners has limited propagation distance from the emitting surface with a drop in energy of 90+% at a distance of 100 cm and are not uniform in their surface coverage area, and do not have the ability to penetrate into biofilm or solid porous or contaminated surfaces.

In another embodiment, the sonotrode may be arranged such that the highly propagating ultrasonic energy generated is able to propagate across a liquid boundary such as water up to a distance of about 50 cm to about 300 cm, or about 100 cm to about 300 cm or about 150 cm to about 300 cm or about 200 cm to about 300 cm to a contaminated surface, transmit uniformly across the whole surface area and volume leaving no single space/zone untouched from the wave energy. In addition, the highly propagating radial waves are able to penetrate up to about 5-20 mm or up to about 5-15 mm or up to about 7-10 mm or into a solid porous or contaminated surface.

In yet another embodiment, the highly propagating ultrasonic energy is emitted substantially at a right angle from the surface of a sonotrode with high energy. In this context high energy refers to a less than about 20% drop in energy and production of shear forces resulting from collapsing cavitation bubbles at a distance of about 100 to about 300 cm from the emitting sonotrode. Furthermore, in this context high energy refers to the ability of the highly propagating ultrasonic energy to propagate into solid or porous surfaces or materials and create cavitation internally up to a depth of about 1-20 mm, or up to a depth of about 2-20 mm or up to a depth of about 5-20 mm or up to about 5-15 mm or up to about 7-10 mm.

In a further embodiment the highly propagating ultrasonic energy enhances the kinetics of thermal conductive heat transfer into biofilms, contaminated materials/surfaces, solid surfaces such as porous oak barrels, microorganisms which normally have very poor thermal conductivity. The highly propagating ultrasonic energy increases the rate of this process up by about 200-300%. In another embodiment the cavitation and sanitizer act synergistically to disinfect, clean and/or remove the biofilm from the surface.

While not being limited by theory it is generally held that highly propagating ultrasonic energy cleans and kills microorganisms via generating cavitation and generating heat. Cavitation comprises the repeated formation and implosion of microscopic bubbles. The implosion generates high-pressure shock waves and high temperatures near the site of the implosion. Heat may also be generated by absorption of the highly propagating ultrasonic energy by the PZT, the horn means, the surface to which the ultrasonic energy is applied and absorption of some of the highly propagating ultrasonic energy by the liquid or gas through which the energy is propagating.

While being limited by theory, it is believed that the application of highly propagating ultrasonic energy generates cavitation and thus shock waves which facilitate penetration of fluid or liquid into a surface. These shock waves combined with locally generated heat at the surface result in the removal of deposits at the surface and also penetrate into the surface to kill microorganisms. The cavitation produced by the ultrasonic energy may also be used to activate specific chemistry (e.g. heat-activated bleach) and hence significantly improve cleaning and disinfection. In addition the application of highly propagating ultrasonic energy can drive fluid components, such as sanitizing agents into the surface to which the ultrasonic energy is applied.

In one embodiment the ultrasonic emitting assembly or ultrasonic generator generates ultrasonic energy at frequencies between about 10 KHz and about 2000 KHz or between about 10 KHz and about 1500 KHz, or between about 10 KHz and about 1000 KHz, or between about 10 KHz and about 750 KHz, or between about 10 KHz and about 400 KHz, or between about 10 KHz and about 250 KHz, or between about 10 KHz and about 125 KHz, or between about 10 KHz and about 100 KHz, or between about 10 KHz and about 60 KHz, or between about 10 KHz and about 40 KHz, or between about 10 KHz and about 30 KHz, or between about 16 KHz and about 30 KHz, or between about 16 kHz and about 22 kHz or between about 19 KHz and about 20 KHz.

In one embodiment the amplitude of the highly propagating ultrasonic energy is between about 0.001 to about 500 microns, preferably between about 0.01 to about 40 microns amplitude, even more preferably between about 1 to about 10 microns.

In one embodiment the energy density of the highly propagating ultrasonic energy is between about of 0.00001 watt/$cm^3$ to 1000 watt/$cm^3$, between about 0.0001 watt/$cm^3$ to about 100 watts/$cm^3$.

In another embodiment the highly propagating ultrasonic energy is applied to a surface over a period of time from about 1 second to about 60 minutes, or from about 5 second to about 50 minutes, or from about 10 seconds to about 40 minutes, or from about 15 seconds to about 40 minutes, or from about 20 seconds to about 30 minutes, or from about 25 seconds to about 20 minutes, or from about 30 seconds to about 10 minutes, or from about 30 seconds to about 1 minute.

Apparatus

In one aspect the invention provides an apparatus for cleaning surfaces by the application of highly propagating ultrasonic energy to those surfaces.

Figure 2:
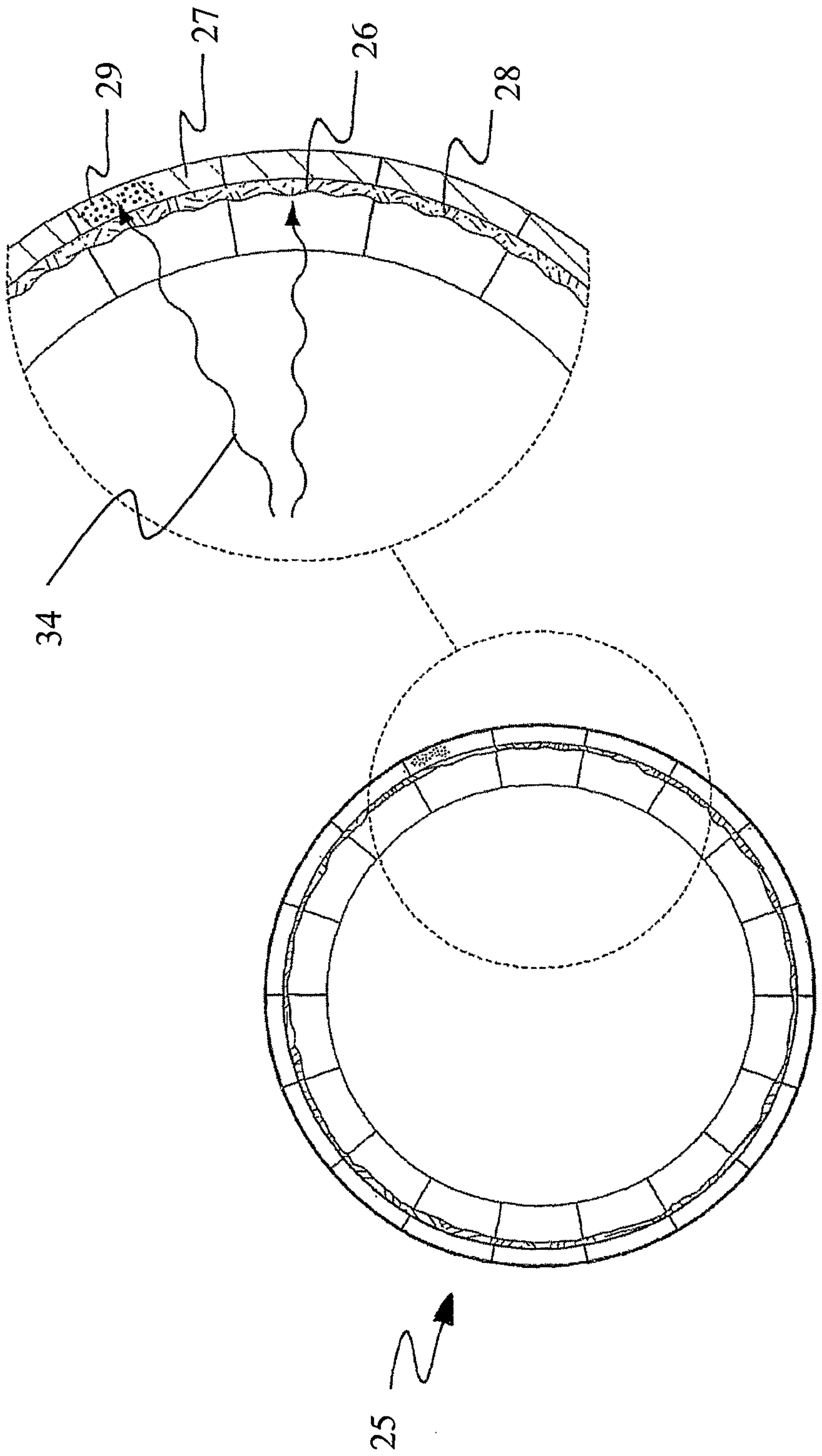
FIG. 2 is a top cross section of a barrel showing the effect of the penetration of the energy waves created by the present invention.
Figure 3:
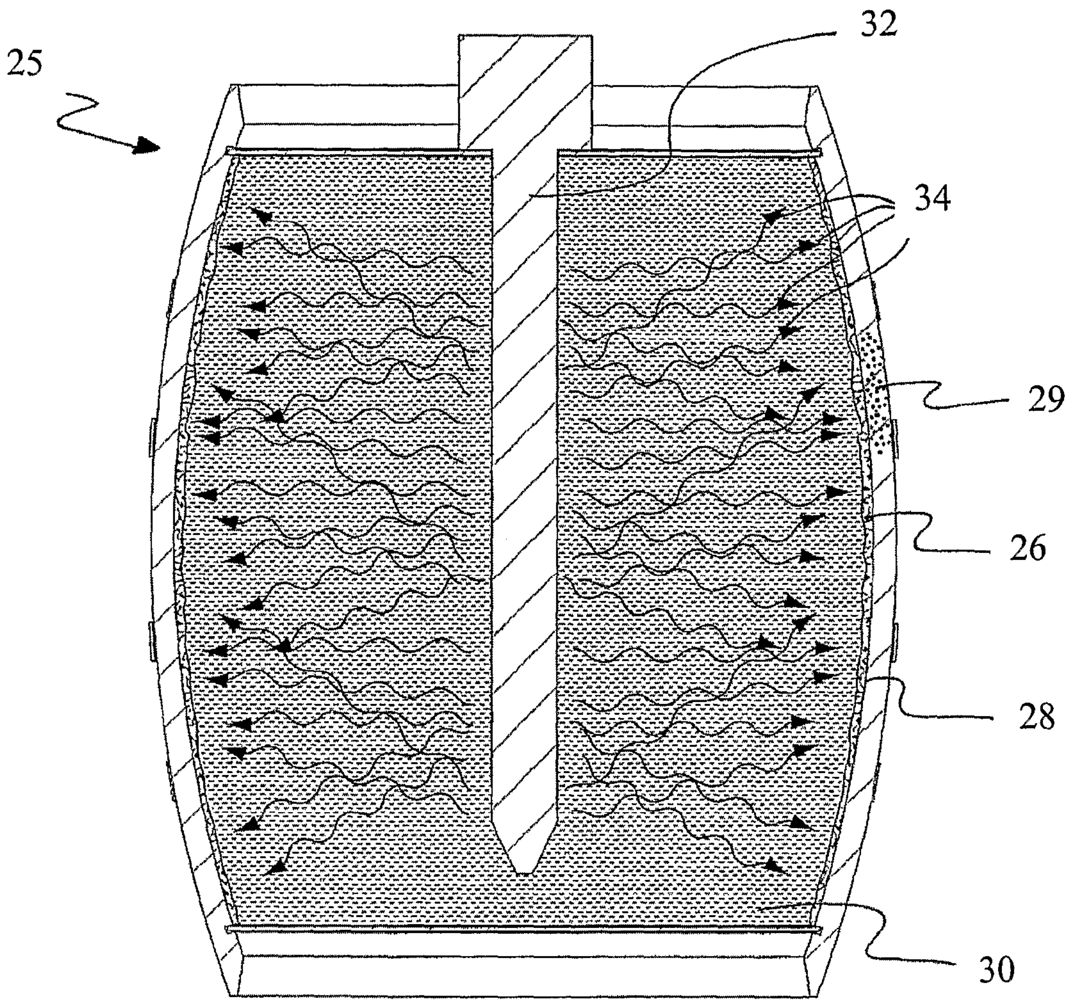
FIG. 3 is a side cross sectional view of a container being cleaned with the present invention.

With reference to FIG. 2 and FIG. 3 a container (such as the wine barrel 25 for illustration purposes), having a layer of detritus, such as tartrate 26, on its inner surface 28, is filled with a fluid 30. Inserted into the fluid 30 is an ultrasonic probe or transducer 32 capable of emitting highly propagating ultrasonic energy 34 applied across the inner surface and which penetrates into the inner surface 28.

The highly propagating ultrasonic energy 34 when at a frequency of between approximately 16-30 KHz enhances mass transfer of fluid 30 behind the tartrate 26 and into the pores inside the wood 27 of the wooden wine barrel 25. The highly propagating ultrasonic energy also results in enhanced convective heat transfer through the tartrate and into the wood 27.

As described herein the highly propagating ultrasonic energy 34 penetrates into the surface 28 and wood substrate 27 and generates cavitation at and within the surface 28 and inside wood substrate 27. The highly propagating ultrasonic energy 34 also penetrates into the surface 28 and wood substrate 27 and is applied to any microorganisms such as *Brettanomyces* 29 present in the wood.

Figure 4:
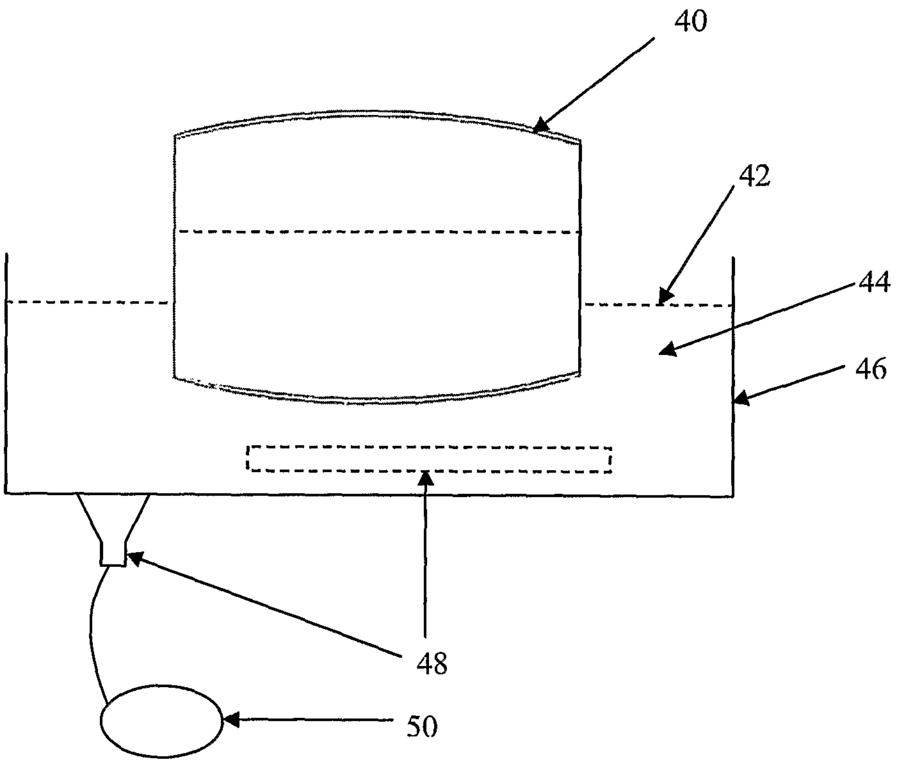
FIG. 4 illustrates a view of a wine barrel complete or with one or both head staves removed, partly or completely filled with water and partly or wholly immersed in a water bath such that the major axis of the barrel is horizontally oriented. Said barrel is then continuously rotated about the major axis whilst ultrasonic energy is applied to the bath water; according to one embodiment of the present invention.
Figure 5:
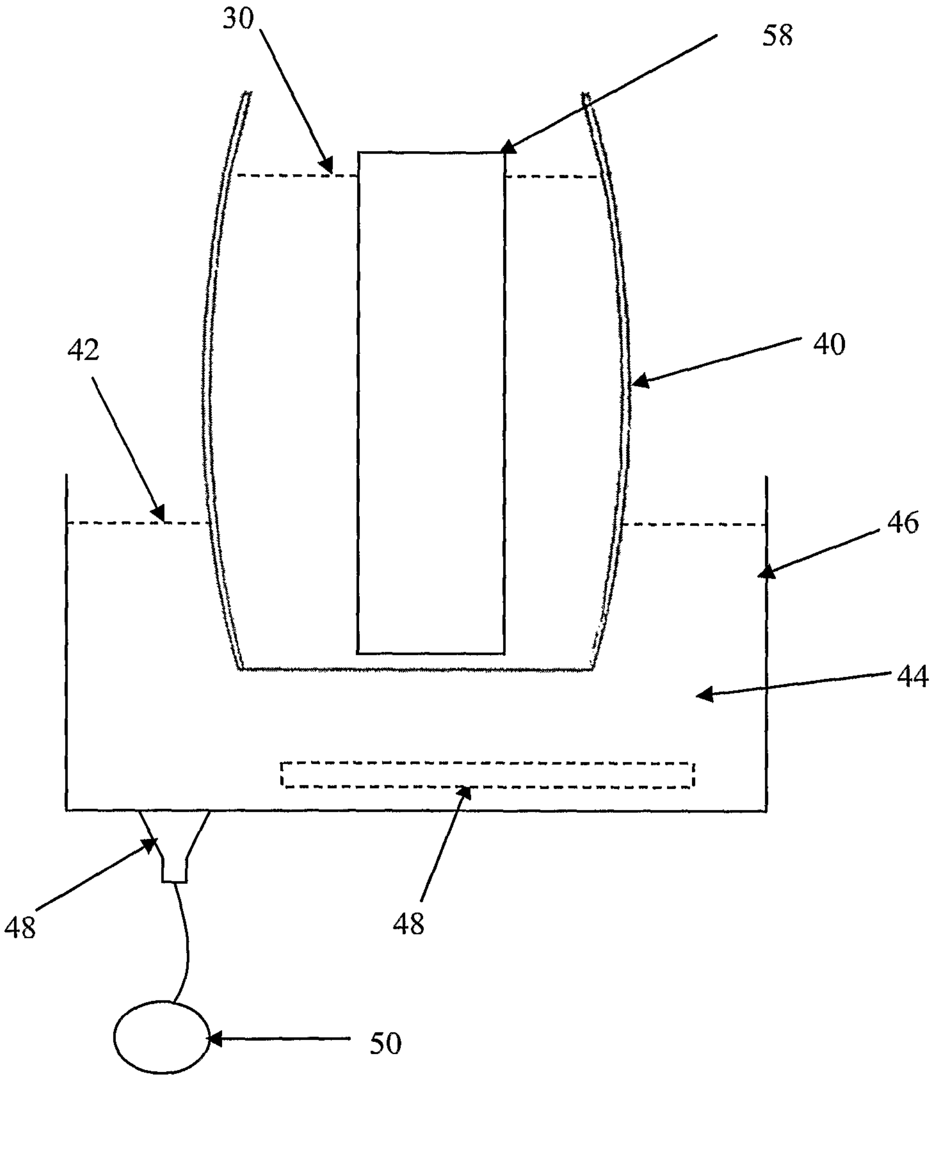
FIG. 5 illustrates a view of a wine barrel, with head stave or modified head stave removed and a sealed polygon sided cylinder of volume equal to between 5% and 95% of the barrel void volume located within the void volume of said barrel, is partly or completely filled with water and partly or wholly immersed in a water bath such that the major axis of the barrel is normal to the plane of the surface of water in the water bath.

With reference to FIG. 4 and FIG. 5 an embodiment of the invention provides a bath for the application of highly propagating ultrasonic energy to surfaces. An emitter assembly may be fixed to the outer walls of a bath or reside within the water contained in said bath.

FIG. 4 illustrates a side cut away view of a partly or wholly immersed container such as a wine barrel 40 at least partially filled with fluid. The wine barrel 40 may be aligned such that its longitudinal axis is substantially parallel to the plane of the resting surface 42 of the bath fluid 44. Highly propagating ultrasonic energy is introduced into the interior of the barrel 40 by way of a plurality of transducer assemblies 5 mounted to the outer surface of the bath 46 or resident within the bath 46. Each transducer assembly 48 is connected to an ultrasonic signal generator 50. The generator 50 produces an ultrasonic signal that is emitted as highly propagating ultrasonic energy by the transducer assemblies 48. The highly propagating ultrasonic energy propagates through the fluid which at least partially fills the barrel 40. In one embodiment the barrel 40 may be continuously or intermittently rotated during the application of the highly propagating ultrasonic energy.

FIG. 5 illustrates a side cut away view of a container such as the illustrated wine barrel 40 with at least one head stave removed and a sealed polygon sided cylinder 3 of volume equal to between 5% and 95% of the barrel void volume of the barrel 1 located within the void volume of said barrel 40. The barrel 40 is at least partly filled with a fluid such as water at least partly immersed in a bath 46 such that the major axis of the barrel is substantially normal to the plane of the resting surface 42 of fluid 44 in bath 46. Highly propagating ultrasonic energy is introduced into interior of the barrel 40 by way of a plurality of transducer assemblies 48 mounted to the outer surface of the bath 6 or residing within the fluid in bath 46. Each transducer assembly 48 is connected to an ultrasonic signal generator 50. The generator 50 produces an ultrasonic signal that is emitted as highly propagating ultrasonic energy by the transducer assemblies 48. The highly propagating ultrasonic energy propagates through the fluid which at least partly fills the filled barrel 40. In one embodiment the barrel 40 may be continuously or intermittently rotated about its major axis during the application of the highly propagating ultrasonic energy.

Figure 6:
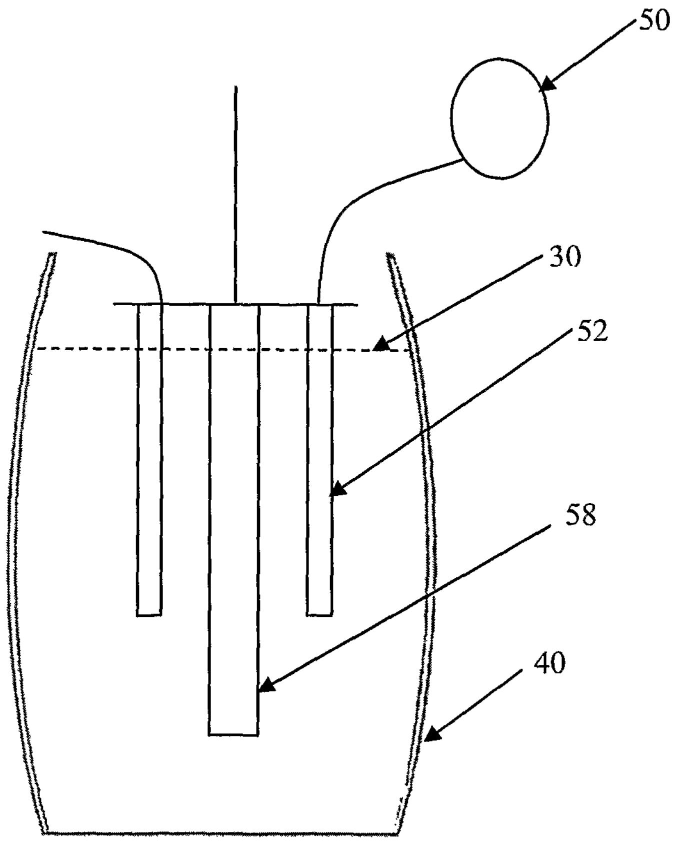
FIG. 6 illustrates a side cut away view of a wine barrel completely or partially filled with water, and has an exemplary plurality of immersible transducer assemblies affixed to a sealed polygon sided cylinder, inserted through the open end of said barrel from which the head stave or modified head stave has been previously removed according to one embodiment of the present invention.
Figure 7:
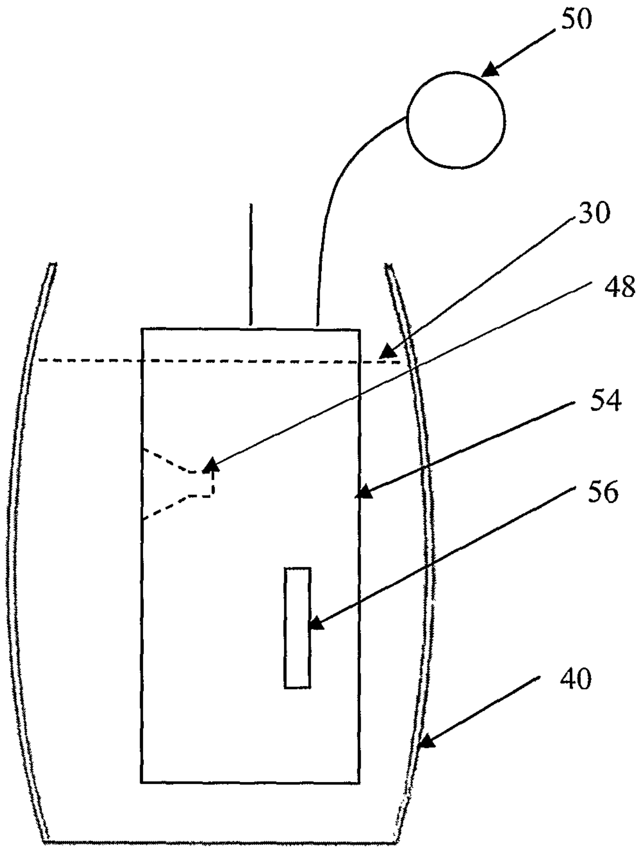
FIG. 7 illustrates a side cut away view of a wine barrel that is completely or partially filled with water and contains an ultrasonic energy emitting device consisting of a plurality of transducer assemblies affixed firmly to the inner surface of a sealed polygon sided cylinder, inserted through the open end of said barrel from which the head stave or modified head stave has been previously removed according to one embodiment of the present invention.

With reference to FIG. 6 and FIG. 7 embodiment of the invention provides apparatus for the application of highly propagating ultrasonic energy to a surface wherein the emitter assembly 52 in FIG. 6 or emitter assembly 54 in FIG. 7, is inserted into the open head of a container such as the illustrated wine barrel 40.

FIG. 7 illustrates a side cut away view of a wine barrel 40 that is completely or partially filled with water and has an attached sensor 56 which monitors the ultrasonic activity within the cavity of the wine barrel 40. This enhances the efficiency of the cleaning by monitoring ultrasonic activity thus enabling the operator to, where necessary, make changes to the process. These changes may include increasing the exposure time that a particular portion of the barrel stave is exposed to the ultrasonic energy.

In another aspect the invention provides an apparatus for cleaning surfaces such as wine barrels using the application of highly propagating ultrasonic energy in which the ultrasonic energy emitting assembly is introduced into an opening in the container. In one embodiment the apparatus allows the cleaning of the barrel in situ, without the barrel having to be moved off site.

FIG. 6 shows an emitter assembly 52 coupled to a polygon sided cylinder 58, suspended within the open head barrel 40. Typically the barrel 40 is at least partially filled with fluid 30, such as water. The polygon sided cylinder 58 is connected to an ultrasonic signal generator 50. The generator 50 produces an ultrasonic signal that is emitted as highly propagating ultrasonic energy by the emitter assembly 52. The highly propagating ultrasonic energy propagates through the fluid which at least partly fills the filled barrel 40 and is applied to the surface of the barrel 40. In a preferred embodiment the emitter assembly 52 comprises stainless steel however the skilled addressee will understand that the emitter assembly 52 is not limited to those comprising or constructed from stainless steel.

As illustrated in FIG. 7, an ultrasonic energy emitting apparatus consisting of a plurality of transducer assemblies 48 mounted to the inner surface of a sealed polygon sided cylinder 54. The apparatus is placed within a container such as the illustrated barrel 40 by inserting it through an open end of said barrel from which at least one head stave has previously been removed. Typically the barrel 40 is at least partially filled with fluid 30, such as water. An ultrasonic generator 50 is connected to the plurality of transducer assemblies contained within the sealed polygon sided cylinder 54. The generator 50 produces an ultrasonic signal that is emitted as highly propagating ultrasonic energy by the emitter assembly by the transducers 48. The highly propagating ultrasonic energy propagates through the fluid 30 which at least partly fills the filled barrel 40 and is applied to the surface of the barrel 40. In one embodiment the barrel 40 may be agitated.

In an alternate embodiment the fluid in the barrel 40 may be agitated either using a pump (not shown) or by rotating or pivoting the sealed polygon sided cylinder 54 within the barrel 40.

FIG. 7 also illustrates a side cut away view of a wine barrel 40 that is at least partially filled with fluid 30 and the apparatus includes an ultrasonic emitter 54 with an attached sensor 56. In one embodiment the attached sensor 56 can move semi independently from the emitter 54. The sensor 56 monitors the highly propagating ultrasonic energy within the wine barrel 40.

It will be understood by the skilled addressee that cables and pipes associated with the apparatus of the present invention are of a sufficient length to enable in situ application of highly propagating ultrasonic energy even when the containers or barrels are at a distance from power or water sources.

In another embodiment of the invention, a pump (not shown) can be used to recirculate or recycle the fluid through a filter, thus limiting the amount of fluid required. In another embodiment fluids such as water may continuously flow through the containers.

The skilled addressee will understand that the present invention is not limited to wine barrels and can be used to clean any container. In particular the invention is useful for cleaning containers with limited access such as liquor barrels, casks, food containers, conduits or equipment that may be at least partially filled with a fluid such as liquor barrels, casks, food containers, bottles. In addition the apparatus of the invention can be used to apply highly propagating ultrasonic energy to for example, food processing equipment, heat exchangers, pipes, valves and foodstuffs such as fruit and vegetables.

Methods Using Apparatus of the Invention

The present invention provides a method of cleaning and/or disinfecting a surface by applying highly propagating ultrasonic energy to a surface of a container. While not being bound by a particular theory it is believed the method works by the action of microscopic cavities collapsing and releasing shock waves, a process known as cavitation. The microscopic cavities are formed by sending highly propagating ultrasonic energy into a fluid that is in contact with the surface to be cleaned and/or disinfected. The microscopic cavities may form on a surface. The shock waves produced by the collapse of the cavities loosen the surface contaminant such as tartrates, biofilms, food residue, microorganisms and the like. This detritus or lees can then be drained by the use of a pump or by inverting the container and allowing the lees to drain out.

In one aspect, the invention provides methods of cleaning a surface, removing a contaminate from and methods of disinfecting a surface by the application of highly propagating ultrasonic energy to said surface.

The use of the apparatus of this invention in the methods of the invention are illustrated herein. For example reference is made to FIG. 2 and FIG. 3, once the barrel 25 is filled with the fluid 30 and the sonotrode 32, capable of providing propagating waves 34, is inserted. The sonotrode 32 is activated at a frequency of between 16-30 KHz. The resulting highly propagating ultrasonic energy 34 generates cavitation in the fluid. Initially the energy created by the cavitation impacts upon the detritus, such as the tartrate 26, but also, surprisingly as described herein by using highly propagating ultrasonic energy at a frequency of between approximately 16-30 KHz (in one embodiment) mass transfer of fluid behind the tartrate 26 and into the pores inside the wood 27 of the wooden wine barrel 25 occurs. The highly propagating ultrasonic energy also results in enhanced convective heat transfer through the tartrate and into the wood 27.

By driving the liquid into the pores of the barrel 25 highly propagating ultrasonic energy 34 can then be transferred into the wood substrate 27 resulting in cavitation inside the wood of the barrel 25. As such, the energy created by the cavitation inside the wood structure has a greater effect on the organisms at or near the surface of the wood, such as any *Brettanomyces* 29 at a depth of up to approximately 20 mm under the inner surface 28 of the wood barrel 25. The cavitation also acts synergistically with the enhanced heat transfer to eradicate spoilage microorganisms such as *Brettanomyces* with greater efficiency and effectiveness than either heat alone or propagating radial energy waves.

The application of highly propagating ultrasonic energy to a surface results in cavitation occurring to the organisms in the wood structure 27 than previously has been possible. This provides the ability to affect a higher level of disinfection or microorganism load reduction in conjunction with cleaning than has previously been possible.

Fluid

In some embodiments the fluid 30 may be a gas or a liquid such as water. In a still further embodiment the liquid is a reverse osmosis purified liquid for example water.

The fluid may be at a temperature of between about 1° C. and about 99° C. or between about 2° C. and about 90° C., or between about 3° C. and about 80° C., or between about 4° C. and about 70° C., or between about 4° C. and about 60° C., or between about 4° C. and about 50° C., or between about 4° C. and about 40° C., or between about 4° C. and about 30° C., or between about 4° C. and about 20° C.

In a preferred embodiment the fluid 30 is at a temperature approximately ≥30° C. but <80° C. even more preferably the fluid 30 is at a temperature of approximately 40° C. to approximately 60° C. These ranges of temperatures are relatively easy to obtain and there is a significantly reduced danger in comparison to techniques that require steam, for example, a temperatures >90° C.

Furthermore, the use of reverse osmosis liquids, such as water, as the fluid improves the effectiveness of highly propagating ultrasonic energy in terms of distance travelled, penetration distance into a porous or solid material and intensity of explosion energy and shear forces released from the formation and collapse of cavitation bubbles. The reverse osmosis water also increases the number of cavitation bubbles formed per $cm^2$ on the contaminated surface and per $cm^3$ in the porous or solid structure. The use of reverse osmosis water also increases the rate of mass transfer of liquid into a solid porous structure such as the wood 27 illustrated in FIG. 2 and FIG. 3 and increases the convective heat transfer into the solid structure thereby improving the load reduction of microorganisms such as *Brettanomyces.*

Furthermore, in embodiments of the invention where the fluid is a liquid such as water the liquid may include one or more optional components such as sanitisers, detergents, deodorisers, flavouring agents, bleaches, antifoaming agents, acids, bases, caustic agents, pH stabilisers, abrasives, surfactants, enzymes, bleach activators, anti-microbial agents, antibacterial agents, bleach catalysts, bleach boosters, bleaches, alkalinity sources, colorants, perfume, soap, crystal growth inhibitors, photo bleaches, metal ion sequestrates, anti-tarnishing agents, anti-oxidants, anti-redeposit ion agents, electrolytes, pH modifiers, thickeners, abrasives, metal ion salts, enzyme stabilizers, corrosion inhibitors, demines, solvents, process aids, perfume, optical brighteners and mixtures thereof.

Removal of Contaminants

The application of highly propagating ultrasonic energy to a surface as illustrated with reference to wine barrels, in particular the internal surfaces of a wine barrel may remove contaminants such as tartrate crystals or biofilms on the surface and suspend them, along with other detritus (referred to as "lees") in the bottom of the barrels. Consequently, in one embodiment the removal of lees facilitates transfer of oak flavour to the wine in recycled oak wine barrels. The methods described herein, when applied to wine barrels provides an interior surface of an oak barrel which is substantially devoid of contaminants and microorganisms which can be detrimental to wine quality.

In some embodiments the methods of the present invention avoid heating of liquids to high temperatures and the use of chemicals. In addition, when the methods of the present invention are used to clean a wine barrel there is less loss of wood flavour compounds compared to high pressure hot or cold water sprays. Consequently, a barrel's life can be extended, thereby reducing the cost of replacing barrels.

In some embodiments the application of highly propagating ultrasonic energy to a surface may occur concurrently with the application of a pulsed electric field to a fluid in contact with the surface. Alternatively the application of highly propagating ultrasonic energy and a pulsed electric field may occur sequentially. In one embodiment the application of highly propagating ultrasonic energy and a pulsed electric field may occur intermittently.

In some embodiments the application of highly propagating ultrasonic energy to a surface may occur concurrently with mechanical brushing of the surface. Alternatively the application of highly propagating ultrasonic energy and mechanical brushing of the surface may occur sequentially. In one embodiment the application of highly propagating ultrasonic energy and mechanical brushing of the surface occurs intermittently.

In one embodiment highly propagating ultrasonic energy of an amplitude of between about 1 to about 10 microns may be applied to the surface of a container, such as a barrel, over a period of about 3 to about 10 minutes.

The present apparatus and methods avoid spoilt wine caused by contamination, improves transfer of oak flavour to the wine through reduced tartrate deposits in the barrels, avoids the loss of oak flavour through existing washing methods, lowers barrel costs by avoiding replacing barrels spoilt by contamination, lowers barrel costs by extending the usable life of barrels, lowers labour costs for cleaning operations, lowers water costs, avoids the of use of chemicals, and lowers water heating costs.

In a further embodiment the present methods avoid spoilt wine caused by contamination, improves transfer of oak flavour to the wine through reduced tartrate deposits in the barrels, avoids the loss of oak flavour through existing washing methods, lowers barrel costs by avoiding replacing barrels spoilt by contamination, lowers barrel costs by extending the usable life of barrels, lowers labour costs for cleaning operations, lowers water costs, avoids the of use of chemicals, and lowers water heating costs.

In one aspect a method of disinfecting the interior surfaces of containers such as barrels and destroying spoilage microorganisms including *Brettanomyces* residing on the surface of the barrel is disclosed.

The practice of recycling wine barrels by way of cleaning is used extensively within the wine industry. However bacterial and yeast contaminations resulting from incomplete cleaning results in increased wine spoilage and consequently increased costs to the wine producer. The difficulty with wine and liquor barrels and other food and beverage containers is that the openings of the containers are restricted. This poses significant problems when such a container is cleaned. Previously the barrels were dismantled and shaved, alternatively high-pressure water or steam has been used to clean such containers. This, however, presents other problems especially in drier areas where winemakers have limited water available and furthermore such methods merely remove surface deposits and do not penetrate into the surface to kill or inactivate microorganisms harboured beneath the surface. The present invention provides the application of highly propagating ultrasonic energy to a surface to clean and disinfect the surfaces, such as the internal surfaces of wine barrels and like containers.

Cleaning and/or Decontamination

In one embodiment, for example as illustrated using the apparatus of FIG. 4 or 5, a method of ultrasonic cleaning introduces the ultrasonic energy into the interior of a container or conduit (illustrated here as a barrel) at least partially filled with a liquid such as water by way of externally generated ultrasonic waves. Ultrasonic energy is applied to the bath water and is transmitted through the barrel staves into the water contained within the barrel wherein the energy released by the collapse of cavitation bubbles created by the ultrasonic energy removes residues and destroys resident micro-organisms.

In one aspect, the methods of the invention may be used to clean and/or disinfect conduits or containers in situ. For example, a conduit fouled by the growth of a biofilm may be at least partially filled with a fluid, such as water. An apparatus of the invention may be introduced into the conduit such that when operated the highly propagating ultrasonic energy propagates through the liquid and is thus applied to the internal surface of the conduit or container to clean and/or disinfect the surface. Lees generated by the method are removed when the fluid is drained from the container. The liquid in the container or conduit may be recirculated or recycled through a filter, thus limiting the amount of water required for the cleaning process. In another embodiment liquids, such as water may continuously flow through the conduits or containers, thus providing a means for the removal of lees from the cleaned or disinfected surfaces.

In one embodiment of the invention sonotrodes which emit highly propagating ultrasonic energy are immersed into open flumes, pipes, vessels, flow through vessels containing a fluid such as water, sanitizer (at various concentrations) and fruit or vegetable products. The fruit/vegetables pass past 1 or more sonotrodes emitting highly propagating ultrasonic energy. The highly propagating ultrasonic energy creates cavitation in the liquid, at the surface of the fruit and vegetables and internally inside the surface tissues of the fruit and vegetables. The residence time of the fruit and vegetable in the ultrasonic field can vary from 0.1 second to 1000 seconds. The flow rate of water and fruits or vegetables can vary from 0.1 liter/min to 10,000 liters/min. The waves and collapsing cavitation bubbles do the following;

1. remove surface bacteria and contamination into the liquid phase where the sanitizer or cleaning agent can get better access to disinfect the micro-organisms. Once in the liquid phase the ultrasound waves and cavitation synergistically drive the sanitizer faster and more efficiently through the outer membranes of the micro-organisms and thus kill them more effectively.

2. the ultrasound waves and cavitation drive more quickly and to a greater penetration depth the sanitizer into the surface structure of the fruit and vegetables where the micro-organisms reside. Internal cavitation causes the sanitizer to work more effectively to penetrate the outer membrane of the micro-organism whilst being inside the fruit or vegetable tissue surfaces.

In one embodiment highly propagating ultrasonic energy of an amplitude of about 1 to about 10 microns may be applied to the surface of a fruit or vegetable over a period of between about 30 to about 1 minute, optionally in the presence of a sanitizer such as chlorine, peroxyacetic acid, ozone or a combination thereof.

For example the vegetables may be selected from the group comprising Amaranth, Beet greens, Broccoli, Bitterleaf, Bok choy, Brussels sprout, Cabbage, Catsear, Celery, Celtuce, Ceylon spinach, Chaya, Chicory, Chinese Mallow, Chrysanthemum leaves, Corn salad, Cress, green beans, Dandelion, Endive, Epazote, Fat hen, Fiddlehead, Fluted pumpkin, Golden samphire, Good King Henry, Jambu, Kai-lan, Kale, Komatsuna, Kuka, Lagos bologi, Land cress, Lizard's tail, Lettuce, Melokhia, Mizuna greens, Mustard, Napa/Chinese Cabbage, New Zealand Spinach, Orache, Pea sprouts/leaves, Polk, Radicchio, Garden Rocket, Samphire, Sea beet, Seakale, Sierra Leone bologi, Soko, Sorrel, Summer purslane, Swiss chard, Tatsoi, Turnip greens, Watercress, Water spinach, Winter purslane, Yau choy. Acorn squash, Armenian cucumber, Eggplant, Bell pepper, Bitter melon Caigua, Cape Gooseberry, Cayenne pepper, Chayote, Chili pepper, Cucumber, Luffa, Malabar gourd, Parwal, Tomato, Perennial cucumber, Pumpkin, Pattypan squash, Snake gourd, Squash (marrow), Sweetcorn, Sweet pepper, Tinda, Tomatillo, Winter melon, West Indian gherkin, Zucchini or Courgette, Globe Artichoke, Squash blossoms, Broccoli, Cauliflower, American groundnut, Azuki bean, Black-eyed pea, Chickpea, Drumstick, Dolichos bean, Fava bean, French bean, Guar, Horse gram, Indian pea, Lentil, Moth bean, Mung bean, Okra, Pea, Peanut, Pigeon pea, Ricebean, Rice, Runner bean, Soybean, Tarwi, Tepary bean, Urad bean, Velvet bean, Winged bean, Yardlong bean, Asparagus, Cardoon, Celeriac, Celery, Elephant Garlic, Florence fennel, Garlic, Kohlrabi, Kurrat, Leek, Lotus root, Nopal, Onion, Prussian asparagus, Shallot, Welsh onion, Wild leek, Ahipa, Arracacha, Bamboo shoot, Beetroot, Black cumin, Burdock, Broadleaf arrowhead, Camas, Canna, Carrot, Cassaya, Chinese artichoke, Daikon, Earthnut pea, Elephant Foot yam, Ensete, Ginger, Gobo, Hamburg parsley, Jerusalem artichoke, Jicama, Parsnip, Pignut, Plectranthus Potato, Prairie turnip, Radish, Rutabaga, Salsify, Scorzonera, Skirret, Sweet Potato, Taro, Ti, Tigernut, Turnip, Ulluco, Wasabi, Water chestnut, Yacón and Yam.

For example the fruit may be fresh or dried and may be selected from the group comprising Apple, Chokeberry, Loquat, Medlar, Pear, Quince, Rose hip, Rowan, Sorb apple, Serviceberry or Saskatoon, Apricot, Chemy, Chokecherry, Greengage, Peach Plum, and hybrids of the preceding species, Raspberries, Blackberry (and hybrids thereof) Cloudberry, Loganberry, Raspberry, Salmonberry, Thimbleberry, Wineberry, Bearberry, Bilberry, Blueberry, Crowberry, Cranberry, Falberry, Huckleberry, Lingonberry, Acal, Barberry, Currant, Elderberry, Gooseberry, Hackberry, Mulberry, Mayapple, Nannyberry Oregon grape, Sea-buckthorn, Sea Grape, Arhat, Batuan, Woodapple, Mango, indian gooseberry, Charichuelo, Cherapu, Coconut, Che, Chinese Mulberry, Cudrang, Mandarin Melon Berry, Silkworm Thorn, Zhe, Durian, Gambooge, Goumi, Hardy Kiwi, Kiwifruit, Mock Strawberry or Indian Strawberry, *Garcinia* dulcis, Lanzones, Lapsi, Longan, Lychee, Mangosteen, Nungu, Grape, (raisin, sultana, or currant when dried), Olive, Pomegranate, Figs, Citrus fruits including Lemon, Orange, Citron, Grapefruit, Kumquat, Lime, Mandarin and Tangerine.

Use of Highly Propagating Ultrasonic Energy and Other Cleaning and Disinfecting Agents As disclosed herein the application of highly propagating ultrasonic energy to a surface results in removal of detritus and/or microorganisms from a surface and from within a surface. Surprisingly, and as disclosed herein, the application of highly propagating ultrasonic energy to a surface together with conventional methods of cleaning and/or sanitising a surface produces improved cleaning and/or sanitising of a surface than would be expected merely from the additive effects highly propagating ultrasonic energy and conventional cleaning and/or sanitising alone. That is, there is a synergistic cleaning and/or effect between the application of highly propagating ultrasonic energy to a surface and the use of conventional cleaning and/or sanitising methods.

Figure 9:
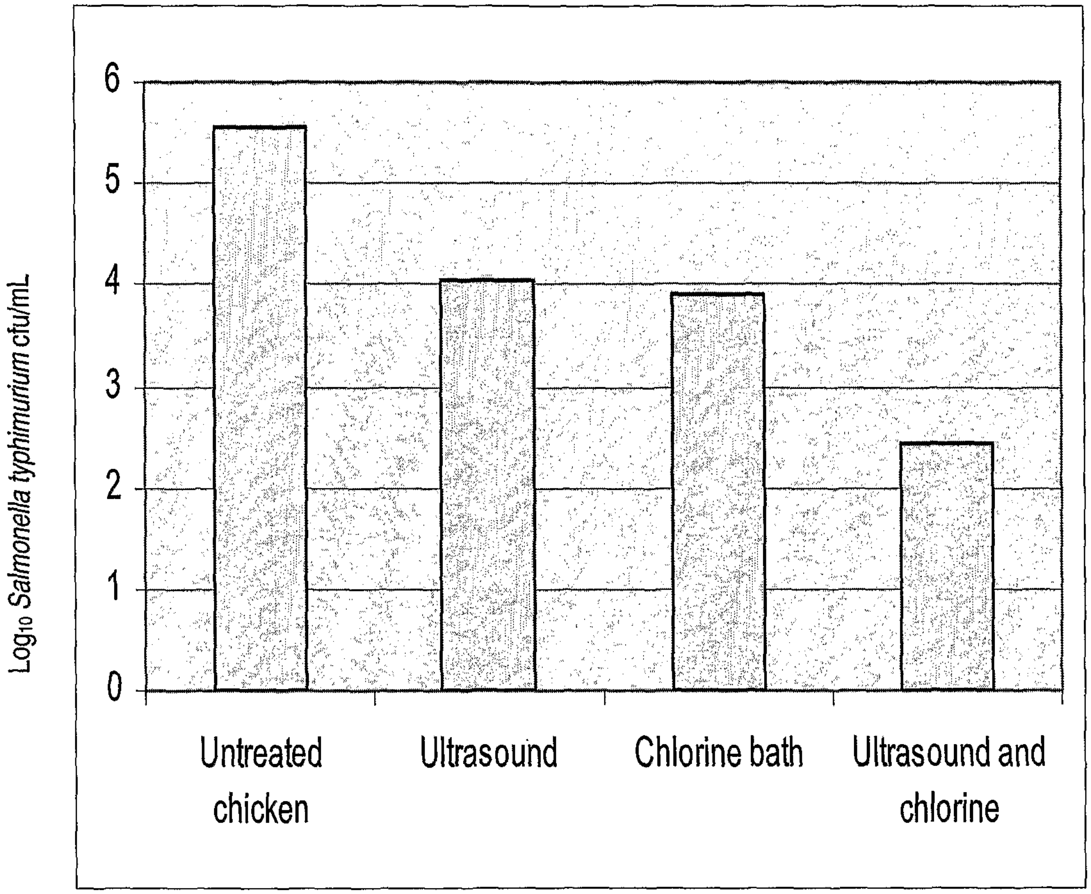
FIG. 9 illustrates the effect of highly propagating ultrasonic energy alone or in conjunction with a chlorine bath compared to the effect of a chlorine bath alone on the levels of *Salmonella typhimurium* on the surface of poultry. A synergistic effect between highly propagating ultrasonic energy and chlorine can be seen.
Figure 10:
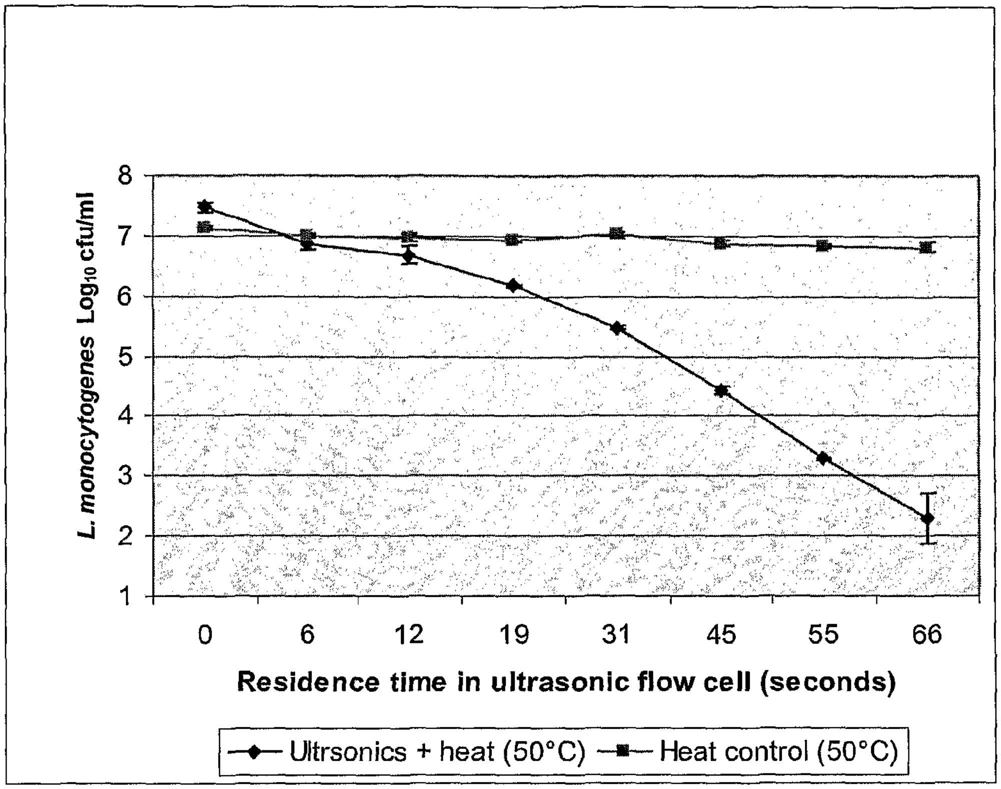
FIG. 10 illustrates the effect of highly propagating ultrasonic energy and heat (50° C.) on the levels of *Listeria monocytogenes* compared to heat (50° C.) alone.
Figure 11:
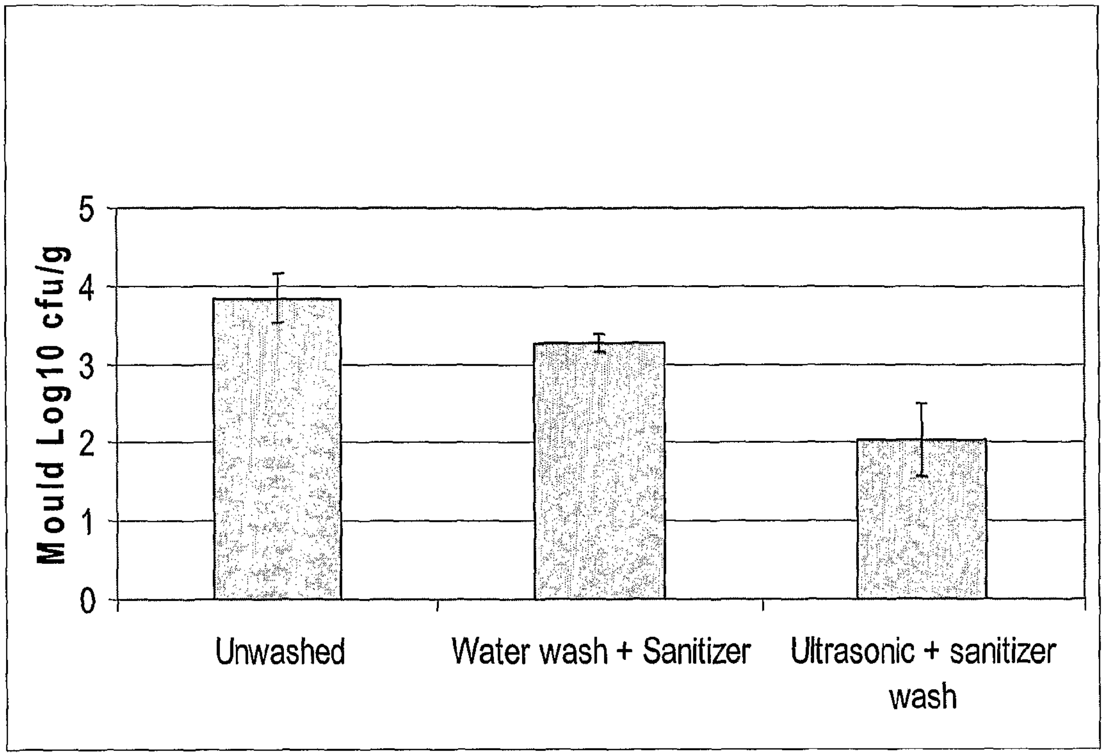
FIG. 11 illustrates the effect of the application of highly propagating ultrasonic energy to the surface of the dried fruit on the levels of fungal spores. A comparison between washing alone, washing with a sanitiser and application of highly propagating ultrasonic energy together with a sanitiser wash is shown.
Figure 12:
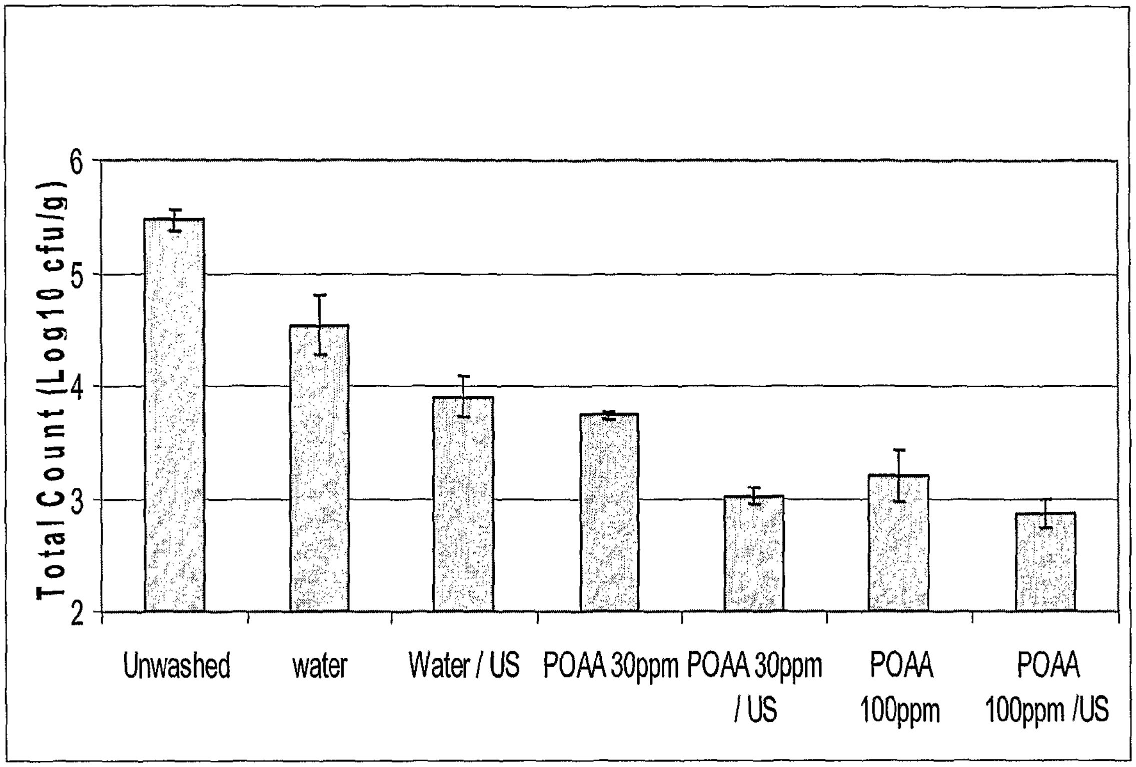
FIG. 12 illustrates the effect of the application of highly propagating ultrasonic energy to the surface of shredded lettuce on microorganism levels. Comparisons between washing alone, washing and highly propagating ultrasonic energy (US), a 30 ppm peroxyacetic acid wash, 30 ppm peroxyacetic acid wash and highly propagating ultrasonic energy (US), a 100 pm peroxyacetic acid wash alone and a 100 ppm peroxyacetic acid wash with highly propagating ultrasonic energy (US) is shown.
Figure 13:
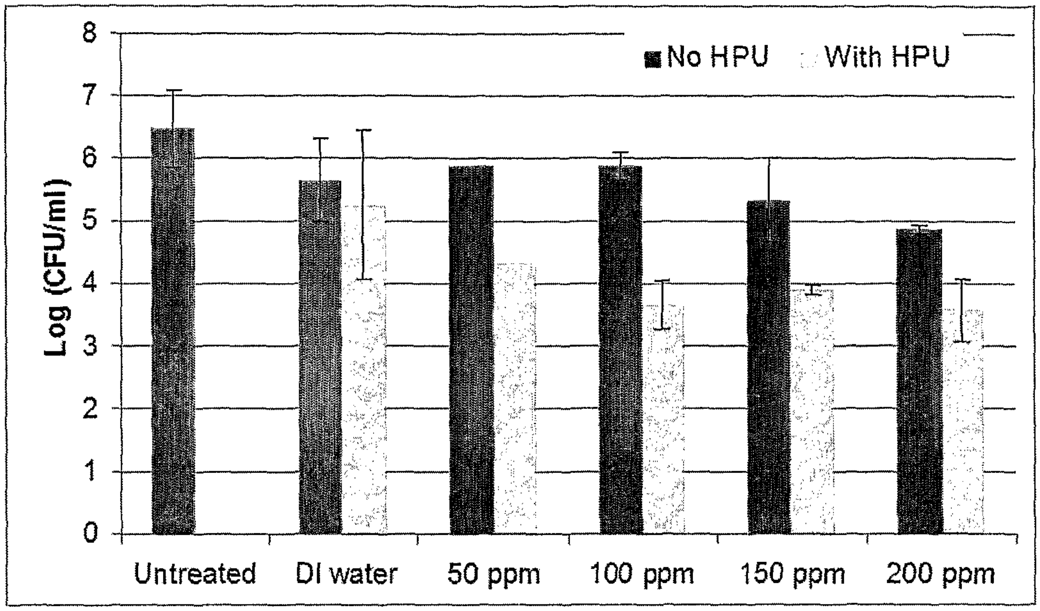
FIG. 13 illustrates the effect of the application of highly propagating ultrasonic energy to the surface of spinach on microorganism levels. Comparisons between deionised water washes and various concentrations of sanitizer (peroxy acetic acid) with and without the application of highly propagating ultrasonic energy (HPU) are shown.

As exemplified herein the application of highly propagating ultrasonic energy to poultry meat in conjunction with a chlorine bath results in a greater reduction of *Salmonella typhimurium* levels compared with either highly propagating ultrasonic energy or a chlorine bath alone (FIG. 9). Similarly sanitisation of shredded lettuce using 30 ppm or 100 ppm together with the application of highly propagating ultrasonic energy provides a greater reduction in total microorganism levels than would be expected from either treatment alone (FIG. 12).

As noted above and while not being limited by theory it is generally held that highly propagating ultrasonic energy cleans surfaces and kills microorganisms by generating cavitation and generating heat. Cavitation comprises the repeated formation and implosion of microscopic bubbles. The implosions generate high-pressure shock waves and high temperatures near the site of the implosion. The shock waves can drive fluid components, such as sanitizing agents into the surface to which the ultrasonic energy is applied thereby increasing the cleaning and/or sanitising effect on a surface than would be expected merely from the additive effects highly propagating ultrasonic energy or the conventional cleaning and/or sanitising when each is performed alone.

The sanitiser may be at least one of ozone, chlorine, peroxy acetic acid, chlorine dioxide, hydrogen peroxide, sodium hydroxide, potassium hydroxide, sodium azide or other commercially available sanitizing formulations, or a combination thereof. The sanitising formulation may be at least one of a detergent, surfactant, soap, bleach, or reactive compound such as sulphamic acid, formic acid, other organic or inorganic acids and the like.

Furthermore the use of reverse osmosis fluids such as water with highly propagating ultrasonic energy greatly increases the kinetics of cleaning or removal of contaminants increases the percentage removal of contamination and enhances the percentage kill of microorganisms at the surface and within the solid structure. The use of reverse osmosis liquids is an improvement over conventional liquids, liquids with chemical additives or degassed liquids. Cleaning effectiveness in reverse osmosis water typically increases by 30% compared with standard potable waters. In addition cleaning time in reverse osmosis water typically is typically reduced by 40%.

In some embodiments the liquid may contain a chemical sanitizer such as ozone, chlorine, peroxyacetic acid, sodium azide. Alternatively or additionally the liquid may contain a cleaning agent such as a detergent, enzyme such as a lipase, surfactant, soap or bleach. Other cleaning and/or sanitizing agents may include caustic soda, potassium hydroxide, sulphamic acid, formic acid, dichromic acid, hydrochloric acid, nitric acid and sulphuric acid. The appropriate concentrations of these agents well known by persons skilled in the art and can be determined by routine experimentation. However, typically concentrations may be in the range of about 1 ppm up to about 500 pmm although higher concentrations may be used.

Organisms

High power ultrasonics kills spoilage microorganisms including spoilage yeasts, such as *Brettanomyces*. This organism and other spoilage yeasts bacteria and moulds can be found in the oak of wine barrels, especially around the inner surface at the interior of the barrel. High power ultrasonic energy heats and disinfects liquid and solid substances and thereby kills organisms found within the oak of barrels to the depth of at least 8 mm while avoiding the use of chemicals, such as sulphur dioxide and ozone.

The methods of the invention may be used to reduce the load of microorganism such as yeasts of the *Brettanomyces* species.

In other embodiments the methods are applicable to the reduction in the load of yeasts of the *Brettanomyces* species and other wine spoilage microorganisms including moulds, yeasts and bacteria. For example wine spoilage yeast may include *Dekkera anomala, Dekkera bruxellensis, Dekkera intermedia, Brettanomyces abstinens, Brettanomyces anomalus, Brettanomyces bruxellensis, Brettanomyces claussenii, Brettanomyces custersianus, Brettanomyces intermedius, Brettanomyces lambicus, Brettanomyces naardensis, Pichia guilliermondii, Piciai membranefaciens, Pichia fermentans, Sachharomycodes ludwidii, Schizosaccharomyces* sp, *Zygosachharomyces* sp including *Z. bailii*, and *Z. bisporus, Hanseniaspora* sp, *Kloeckera* sp, *Hansenula* sp., *Metschnikowia* sp, *Torulaspora* sp, or *Debaryomyces* sp.

In other embodiments the yeast may be a film yeast such as *Candida vini, Candida mycoderma* or *Candida krusei*. The wine spoilage mould may include *Aspergillus* sp or *Penicillium* sp.

For example wine spoilage bacteria may include *Acetobacter* species such as *Acetobacter pasteurianus, Acetobacter liquefasciens, Acetobacter aceti, Acetobacter rancens, Gluconacetobacter* species such as, *Gluconobacter oxydans, Lactobacillus* species such as *Lactobacillu plantarum, Lactobacillus brevis, Lactobacillus fructivorans* (formerly *Lactobacillus trichoides*), *Lactobacillus hilgardii, Lactobacillus kunkeei, Lactobacillus buchneri, Lactobacillus fermentatum, Lactobacillus cellobiosis, Lactobacillus collonoides, Lactobacillus plantarum, Leuconostoc* species such as *Leuconostoc oeno, Pediococcus* species such as *Pediococcus damnosus, Pediococcus pentosaceus, Pediococcus parvulis* and *Oenococcus oeni*

The methods of the invention may be used to reduce the load of microorganisms such as moulds, yeasts and bacteria on foodstuffs, in particular fresh fruit and vegetables. The food spoilage microorganisms may include yeasts, moulds and bacteria. For example the spoilage yeasts may include *Saccharomyces* sp, *Zygosaccharomyces* sp, *Rhodotorula* sp. The fungal spoilage organisms may be *Botrytis cinerea, Penicilliumi* sp. such as *P. digitatum, Fusarium* sp., *Guignardia bidwellii, Sclerotinia sclerotiorum, Aspergillus niger*. The spoilage bacteria may be *Salmonella typhimurium, Escherichia coli, Clostridium botulinum, Staphylococcus aureus, Listeria monocytogenes, Erwinia* sp, such as *E. carotovora, Bacillus subtilis, Acetobacter, Enterobacter aerogenes, Micrococcus* sp such as *M. roseus, Rhizopus* sp. such as *R. nigricans, Alcaligenes, Clostridium, Proteus vulgaris, Pseudomonas fluorescens, Lactobacillus, Leuconostoc, Flavobacterium.*

The methods of the invention may be used to reduce and or remove biofilms from a surface. Biofilms may be generated by the growth of a number of microorganisms including bacteria, archaea, protozoa, fungi and algae. Bacterial components of biofilms may include, for example *Proteus mirabilis, Pseudomonas aeruginosa, Streptococcus mutans, Streptococcus sanguis* or *Legionella* sp.

EXAMPLES

Example 1

Tartrate Removal and *Brettanomyces* Reduction in Oak Wine Barrels

Conventional ultrasonic technology is ineffective for tartrate removal and *Brettanomyces* reduction on oak staves contaminated with the same amount of tartrate and *Brettanomyces* organism compared to the methods and apparatus of the present invention. 2 inch oak coupons were contaminated at 2 mm depth with known amount/concentration counts of *Brettanomyces* microorganisms were placed in a 10 liter water bath at 40°. The contaminated coupons were sonicated using the three different methods shown in the table below for 1 minute. Coupons were then removed and plated.

TABLE 1

| Tartrate removal and Brettanomyces reduction | | | |
|---|---|---|---|
| | Sonotrode type | % Surface tartrate removal (10 minutes) | Brett. kill 2 mm in oak |
| 1 | Conventional sonotrode for liquid immersion | <5% | 0% |
| 2 | Conventional ultrasonic cleaning - bath | 0% | 0% |
| 3 | Highly propagating ultrasonic energy | 100% | 100% |

Table 1 clearly shows the increased efficacy of the ability of the method of the present invention to kill micro-organisms embedded within the structure of the container. This results in a greater ability to remove the infecting organism from the container thus greatly reducing the chance of the organism re-establishing itself in the container.

As would now be apparent to those skilled in this art, the above invention may be applied to any porous material or organic material that either requires disinfection on both the surface and subsurface. Such a method is applicable, for example, to porous materials such as fruits or vegetables capable of withstanding the conditions as generally outlined.

Example 2

Biofilm Removal

An apparatus of the present invention was used to treat a 700 mm diameter pipe. A *Proteus mirabilis* biofilm was present on the internal surface of the pipe and *Listeria* sp, were known to be a component of the biofilm. The pipe was filled with water and an apparatus of the invention introduced into the water such that when operated highly propagating ultrasonic energy propagates through the liquid and is applied to the internal surface of the pipe.

TABLE 2

| Biofilm removal | |
|---|---|
| Ultrasonic Frequency | % Bio-film Removal |
| 350 kHz | 33% |
| 150 kHz | 56% |
| 33 kHz | 68% |
| 20 kHz | 100% |

As shown in Table 2, highly propagating ultrasonic energy at wavelengths of 350 kHz, 150 kHz, 33, kHz and 20 kHz was tested and it can be seen that ultrasonic energy of 20 kHz results in 100% biofilm removal. The highly propagating ultrasonic energy was applied to the biofilm for 1 minute.

The use of hot water at 85° C. with a caustic agent typically shows less than 90% reduction in biofilm reduction which results in residual biofilm that can recolonise the pipe surface after cleaning. However, the use of hot water at 85° C. with a caustic agent (50 ppm NaOH) and the application of highly propagating ultrasonic energy at 20 kHz results in 100% removal of biofilm organisms. That is, after treatment no *Proteus* or *Listeria* could be detected from the treated areas of the pipe.

Example 3

*Brettanomyces* Reduction in Oak Surfaces

Using laboratory-infected oak blocks attached to the staves of barrels allowed testing to be performed under controlled conditions and enabled comparison of the treatments against controls. Blocks were cut from new American oak staves, as well as uninfected and tartrate-free staves of used one and three-year old American oak barrels previously cleaned by high pressure hot water. The sterilised blocks were infected by suspending them in an actively growing liquid culture of *Dekkera bruxellensis* strain AWRI 1499 (*Brettanomyces*).

A commercial standard static spray head was used to deliver HPHW (1000 psi/60° C.) or MPHW (70 psi/60° C.) through the bung-hole of the barrel. A water temperature of 60° C. was chosen as the benchmark as it is the most commonly used temperature in the wine industry. A highly propagating ultrasonic energy apparatus was used to apply highly propagating ultrasonic energy to the surface of the infected oak blocks in a barrel filled with 60° C. reverse osmosis water.

'Sliced Block' Method

A method was developed to enable studies to be carried out on the efficacy of highly propagating ultrasonic energy, HPHW and MPHW to inactivate *Brettanomyces/Dekkera* cells present on the surface of a stave, as well as at a depth of 2 mm. Whole new American oak staves (27 mm thick, medium+toast) were cut into blocks approximately 60 mm in length, and a 4 mm hole drilled in their centre to allow fixing of the 'sliced blocks' to the barrel during HPHW and MPHW treatment. Each block was then sawn in the same plane as the toasted surface to yield two pieces of wood—a 2 mm thick slice containing the toasted surface and a 25 mm thick slice. Each 2 mm slice and its corresponding 25 mm slice were labeled near the drilled holes using a marker pen, wrapped together tightly in aluminum foil and then sterilised by autoclaving. A second autoclaving occurred after the slices had been left overnight to allow germination of any spores surviving the initial autoclaving. The sterile 2 mm slices were then threaded in groups of 12 onto surface-sterilised (70% v/v ethanol-dipped) lengths of nylon fishing line and immersed into the vigorously growing *Brettanomyces/Dekkera bruxellensis* broth culture for 12 days.

Sterilised stainless steel washers were fixed to each group of 2 mm slices to ensure that they remained evenly submerged in the culture. Following removal from the infection culture, the 2 mm slices were gently jiggled in 2×10 L vessels of sterile saline to remove 'unbound' cells. The 2 mm slices were then re-assembled with their pre-sterilised corresponding 25 mm slices using a single sterile staple along the wood grain on one side. A sterilised 30 mm-wide rubber band was wrapped around each assembled unit to prevent penetration of the highly propagating ultrasonic energy and hot water from the cut sides of the block during treatment. Finally, a piece of surface sterilised parafilm was wrapped around the sides of the assembled sliced blocks to hold everything in place. Each assembled sliced block was stored in sterile 500 mL bags until required.

Treatment of Infected Sliced Blocks with Highly Propagating Ultrasonic Energy and HPHW For highly propagating ultrasonic energy treatment each assembled sliced block was aseptically transferred onto a surface-sterilised steel bracket with the 2 mm slice facing outwards and then submersed to the depth of the bilge in a water-filled barrel. For HPHW treatment the assembled sliced blocks were aseptically affixed to the bilge region of the barrel with sterilised stainless steel screws after removing a headstave. After replacing the headstave, HPHW was applied with a standard commercial static spray head.

Following treatment, all assembled sliced blocks were aseptically transferred to separate sterile 500 mL bags. The sliced blocks were treated at 60° C. with highly propagating ultrasonic energy for five, eight or 12 minutes or with HPHW for three, five or eight minutes. Following treatment, the 2 mm slice was separated from its corresponding 25 mm slice, and the front (top surface) and back (representing a subsurface depth of 2 mm) swabbed (Quick Swabs, 3M™). Swab areas (area 3.46 $cm^2$) were defined by the random placement of two sterilised stainless steel washers (21 mm ID) on the surface of the slice. Dilutions of each swab in sterile saline were plated onto Wallerstein's Laboratory Nutrient Agar, supplemented with 2 mg/L cycloheximide.

All swab plates were incubated at 25° C. for 12 days prior to counting. Initial cell numbers on the surfaces of the 2 mm slices yielded an average of 7000±4000 colony-forming units (cfu) per mL per $cm^2$ oak wood surface. This study found that 100% of the cells on the surface and at 2 mm were inactivated following highly propagating ultrasonic energy and HPHW treatments at all time points.

Treatment of Infected Sliced Blocks with HPHW and MPHW

This study was carried out to determine if HPHW and MPHW would have the same effect on *Brettanomyces/Dekkera* cells present in different parts of the barrel. The sliced blocks were aseptically affixed to the inside of the barrel with sterilised stainless steel screws in four positions. One sliced block was affixed to the headstave and another to a stave directly opposite the bung-hole. After replacing the headstave, HPHW or MPHW was applied with a standard commercial static spray head. The sliced blocks were treated for three, five and eight minutes with HPHW and MPHW. Following treatment, only the surface (top) of the 2 mm slice was swabbed using 3M Quick Swabs. Initial cell numbers on the surfaces of the 2 mm slices yielded an average of 2700±400 colony forming units (cfu) per mL per $cm^2$.

Greatest reduction in cell numbers was achieved at the headstave and directly opposite the bung-hole, although after three minutes' treatment with MPHW and HPHW, the percent inactivation was only 11.5% and 48.8%, respectively. With longer treatment times, fewer viable *Brettanomyces/Dekkera* cells were detected in those positions. In contrast to highly propagating ultrasonic energy (see above) where 100% of *Brettanomyces/Dekkera* cells on the surface and at 2 mm of sliced blocks opposite the bong hole were inactivated by HPHW treatments. However, in this study, only 99.8% were killed after eight minutes. HPHW and MPHW treatment of sliced blocks located in positions the headstave and the position opposite the bunghole showed extremely variable results. Percent inactivation in the intermediate positions ranged from 82-100% and 0-99%. The ability of HPHW and MPHW to kill viable *Brettanomyces/Dekkera* cells in a barrel is highly dependant on their location. Viable cells present on the barrel head and bilge region (opposite the bung hole) appear most vulnerable whereas those present in other regions of the barrel have greater chances of survival.

Treatment of Infected One- and Three-Year-Old Staves with Highly Propagating Ultrasonic Energy and HPHW (1000 psi/60° C.)

Stave pieces (10×5 cm) were cut from tartrate-free one- and three-year-old staves (American oak, medium toast), sterilised by autoclaving and then immersed in YPD medium (300 mL) containing 0.01% (w/v) cycloheximide. *Dekkera bruxellensis* (5×107 cells/mL) was directly inoculated into this medium and incubated at 30° C. for five days. The stave pieces were then removed from the medium and immediately used for the respective trials. After treatment, the samples were refrigerated overnight (4° C.) and processed the following day. Triplicate core samples were taken from each treated and control stave, and 2 mm slices to a depth of 4 mm were removed.

The slices were milled in 50 mL of 0.9% saline (IKA A11 grinder, Crown Scientific) using a method previously shown not to affect cell viability (data not shown). The suspensions were centrifuged, the supernatant removed and the pellet re-suspended in 0.9% saline (1 mL). Aliquots of 10 μL were plated onto YPD agar and incubated to determine cell counts. In this study, the number of viable *D. bruxellensis* cells present on the surface (2 mm slice) and sub-surface (4 mm slice) of infected staves after five, eight, 12 minutes' exposure to highly propagating ultrasonic energy in a barrique containing water at 60° C. was determined and compared with the effect of HPHW treatment for three, five and eight minutes on one-year-old infected staves. The infected stave pieces for highly propagating ultrasonic energy treatment were attached to the barrel staves in the region of the bilge. Cell counts were expressed as colony forming units per the volume of the 2 mm core sample slice (approximately 142 $mm^3$).

Figure 8:
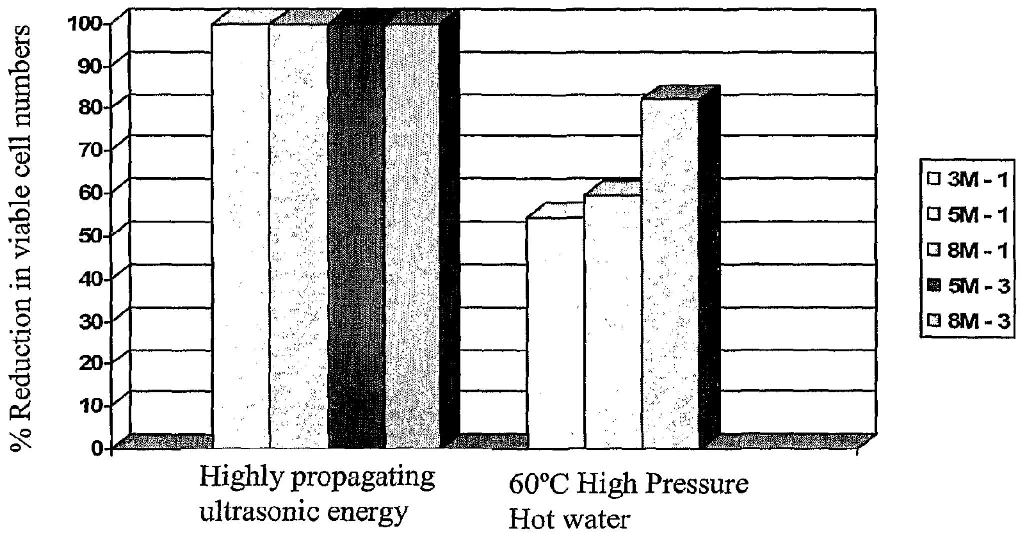
FIG. 8 illustrates the reduction of viable *Brettanomyces bruxellensis* cells (AWRI strain 1499) in sub-surface (2-4 mm) of infected 1- & 3-year old oak staves, compared to the control sample, using highly propagating ultrasonic energy at 60° C., and high pressure hot water (1000 psi at 60° C.).

The reduction of viable *Dekkera bruxellensis* cells (AWRI strain 1499) in the surface slice (0-2 mm) and sub-surface slice (2-4 mm) of infected one- and three year-old oak staves, compared with the control sample, using highly propagating ultrasonic energy and HPHW are summarised in FIG. 8. Initial cell populations in the surface slice for treatment by highly propagating ultrasonic energy were 5974 and 4512 cfu/$mm^3$ for the one- and three-year old staves, respectively. No viable cells were detected at any time at 60° C., suggesting that highly propagating ultrasonic energy treatment was effective in deactivating all viable cells in one- and three-year old infected wood.

The number of cells detected at 2-4 mm below the surface of the control stave for the one and three-year old infected staves was 18.5 and 84.0 cfu/$mm^3$, respectively, highly propagating ultrasonic energy at 60° C. destroyed all the cells. Surface and sub-surface slices of one year infected staves were exposed to HPHW for three, five and eight minutes. The surface and sub-surface control staves contained 8129 and 20 cfu/$mm^3$, respectively.

Although significant reduction in cell numbers occurred in the surface slices after all treatment times, at no time was total elimination of cells achieved, unlike that seen to occur in the highly propagating ultrasonic energy trials at 60° C. Further, there was no consistent trend in the reduction of numbers of viable cells with increasing time of HPHW exposure. Although some reduction in cell numbers was achieved in the subsurface (2-4 mm depth), total elimination was not achieved, again, unlike the case for the highly propagating ultrasonic energy treatments. The data does, however, suggest a decrease in the number of viable cells with increased time of exposure to hot water.

Discussion and Conclusion

The efficacy of highly propagating ultrasonic energy treatment in reducing numbers of *Dekkera bruxellensis* cells on the surface and sub-surface of barrel wood has been demonstrated in the present studies. Infected new, one and three-year-old staves were used to compare barrel sanitising techniques currently applied in wineries (hot water washes at high and mains pressures). Viable cells were dramatically reduced (>1000× reduction) on the surface of wood of all ages studied with total inactivation occurring most successfully at 60° C. with five-minute highly propagating ultrasonic energy exposure. Although sub-surface infection numbers were much lower in the control staves, highly propagating ultrasonic energy exposure on these samples also showed reduction in cell numbers for all ages of wood. The combination of highly propagating ultrasonic energy and temperature was 60° C. for five minutes, which yielded a greater than 1000-fold reduction. These studies have also clearly established that the present and most widely adopted cleaning technique of applying high pressure or mains pressure hot water sprays to the interior of barrels does not completely inactivate *Brettanomyces/Dekkera* cells. Further, the location of viable cells within the barrel environment determines their chances of survival, with populations within the arc of the barrel between the head stave and bilge having the greatest opportunity to survive and proliferate.

Example 4

Synergistic Cleaning and Disinfection of Food Products by Application of Applying Highly Propagating Ultrasonic Energy to Surface of Food Products Food products including spinach, sprouts, orange, melon, apple and tomato were sampled before treatment and plated to determine known amount of total bacteria on the untreated samples as shown in Table 3.

Sanitizers such as peroxyacetic acid or chlorine were prepared in water at the concentrations indicated in Table 3. The solutions were then cooled to 4° C. The volume of the sanitizer/water solution used in this Example was 2.0 L. 500 g quantities of the food products were added to the cooled solutions of water/sanitizer and mixed for 60 seconds using a slow speed mechanical agitator. Samples were then taken from the surface of the food product and plated.

The same process was repeated with the application of highly propagating ultrasonic energy to the surface of the food products suspended in the solutions of water/sanitizer. The highly propagating ultrasonic energy was emitted from a sonotrode inserted into the suspension of water/sanitizer and food product for a period of 60 seconds. The power setting used was 400 Watts.

Table 3 clearly demonstrates the synergistic effect when highly propagating ultrasonic energy is combined with chemical sanitizer to give a greater log reduction in total bacteria plate counts on the surface of food products. At all sanitizer concentrations and types of sanitizer used, the amount of log reduction in total bacteria levels was greater when using ultrasound/sanitizer as compared to sanitizer alone.

TABLE 3

Results on cleaning disinfection of food products.

| Food Product | Control log counts before treatment Total bacteria plate count | Sanitizer and concentration used. | Log reduction with sanitizer only | Log reduction with sanitizer and ultrasound |
|---|---|---|---|---|
| spinach | 6.5 | Peroxyacetic acid | | |
| | | 50 ppm | 0.9 | 1.5 |
| | | 100 ppm | 1.3 | 2.4 |
| | | 200 ppm | 1.6 | 3.0 |
| spinach | 6.4 | Chlorine | | |
| | | 50 ppm | 0.8 | 1.4 |
| | | 100 ppm | 1.0 | 2.2 |
| | | 200 ppm | 1.3 | 2.8 |
| sprouts | 6.0 (*Listeria* bacteria) | Peroxyacetic acid | | |
| | | 100 ppm | 1.8 | 3.2 |
| oranges | 5.8 | Chlorine | | |
| | | 100 ppm | 1.7 | 3.1 |
| | | 200 ppm | 2.1 | 3.7 |
| melon | 6.7 | Chlorine | | |
| | | 50 ppm | 0.9 | 1.6 |
| | | 100 ppm | 1.4 | 2.5 |
| | | 200 ppm | 2.0 | 2.9 |

TABLE 3-continued

Results on cleaning disinfection of food products.

| Food Product | Control log counts before treatment Total bacteria plate count | Sanitizer and concentration used. | Log reduction with sanitizer only | Log reduction with sanitizer and ultrasound |
|---|---|---|---|---|
| apples | 5.8 | Ozone | | |
| | | 50 ppm | 1.4 | 2.5 |
| tomato | 5.5 | Chlorine | | |
| | | 100 ppm | 1.0 | 2.0 |
| | | 200 ppm | 1.4 | 2.9 |

The invention claimed is:

1. A method of cleaning, disinfecting or removing a contaminant from a surface, or any combination thereof, by applying highly propagating ultrasonic energy to said surface, the method comprising:

immersing at least a portion of the surface into a fluid, wherein said fluid is in contact with, or is brought into contact with an assembly comprising at least one ultrasonic sonotrode; and emitting highly propagating ultrasonic energy from said at least one sonotrode to generate cavitation at the surface thereby cleaning, disinfecting or removing a contaminant from said surface; and wherein the highly propagating ultrasonic energy is emitted substantially orthogonal to the axial direction of a sonotrode.

2. The method of claim 1, wherein the contaminant is a microorganism, biofilm, scale or tartrate.

3. The method of claim 1 for ultrasonic cleaning of a surface of a first container, the method comprising:

placing a fluid in contact with at least a portion of the surface of the first container wherein said fluid is contained within a second container, and placing said at least one sonotrode in contact with said fluid or in contact with a surface of said second container;

emitting highly propagating ultrasonic energy from said at least one sonotrode; and applying said energy to clean the surface of the first container.

4. The method of claim 3, further comprising rotating the first container relative to the second container to place the fluid in contact with another portion of the surface of the first container.

5. The method of claim 1 for cleaning a surface having detritus, the method comprising:

introducing the surface to a fluid;

introducing the assembly to the fluid;

emitting highly propagating ultrasonic energy from said assembly during rotation of the surface to expose the surface layers of the inner surface to ultrasonic energy; and applying said energy to remove detritus from said surface.

6. The method of claim 5, wherein the surface is present in a container.

7. The method of claim 6, wherein the container is a barrel, optionally a wooden wine barrel.

8. The method claim 5, wherein the detritus comprises a biofilm, a spoilage microorganism, food product residue, wine residue, tartrate, scale or any combination thereof.

9. The method of claim 8 wherein the spoilage microorganism is a species of the *Brettanomyces* genus.

10. The method of claim 1, wherein the emitting assembly creates cavitation within the fluid.

11. The method of claim 10, wherein said cavitation generates heat in the fluid, or enhances heat transfer into said surface or contaminant or both said surface and contaminant, or generates heat in the fluid and enhances heat transfer into said surface or contaminant or both said surface and contaminant.

12. The method of claim 1, wherein the fluid contains a chemical sanitizer and/or a cleaning agent.

13. The method of claim 1, further comprising the step of applying a pulsed electric field to the fluid.

14. The method of claim 1, further comprising the step of mechanical brushing of the surface.

15. The method of claim 1, further comprising positioning said at least one sonotrode in communication with a transducer.

* * * * *